US005342346A

United States Patent [19]
Honda et al.

[11] Patent Number: 5,342,346
[45] Date of Patent: Aug. 30, 1994

[54] FLUID CONTAINER

[75] Inventors: Minoru Honda, Otsu; Masanobu Iwasa, Osaka; Tetuzi Miyamoto, Otsu; Koji Ikeda, Osaka; Toshihiro Kikuchi, Suita, all of Japan

[73] Assignee: Nissho Corporation, Osaka, Japan

[21] Appl. No.: 44,481

[22] Filed: Apr. 9, 1993

[30] Foreign Application Priority Data

Apr. 10, 1992 [JP] Japan .................................. 4-118036
Apr. 24, 1992 [JP] Japan .................................. 4-132023

[51] Int. Cl.$^5$ ......................... A61B 19/00; A61M 5/32
[52] U.S. Cl. .................................... 604/413; 604/411; 604/412; 604/414; 604/415; 604/56; 604/82; 604/84; 604/86; 604/87; 604/88; 604/92
[58] Field of Search ................. 128/912; 220/254–256

[56] References Cited

U.S. PATENT DOCUMENTS

| | | | |
|---|---|---|---|
| 611,520 | 9/1898 | Smith . | |
| 2,636,493 | 4/1953 | Lockhart . | |
| 2,653,609 | 9/1953 | Smith . | |
| 2,659,370 | 11/1953 | Smith . | |
| 3,917,063 | 11/1975 | Chibret et al. . | |
| 3,932,222 | 1/1976 | Dorn . | |
| 3,995,630 | 12/1976 | Van de Veerdonk | 604/202 |
| 4,092,546 | 5/1976 | Larrabee . | |
| 4,234,083 | 11/1980 | Cohen . | |
| 4,583,971 | 4/1986 | Bocquet et al. . | |
| 4,614,267 | 9/1986 | Larkin . | |
| 4,757,911 | 7/1988 | Larkin et al. . | |
| 4,927,013 | 5/1990 | Brunt et al. . | |
| 4,936,841 | 6/1990 | Aoki et al. | 604/413 |
| 4,982,875 | 1/1991 | Pozzi et al. | 604/416 |

FOREIGN PATENT DOCUMENTS

| | | |
|---|---|---|
| 0225468 | 6/1987 | European Pat. Off. . |
| 0431779 | 6/1991 | European Pat. Off. . |
| 2006010 | 4/1969 | France . |
| 63-135642 | 9/1988 | Japan . |
| 2-26506 | 6/1990 | Japan . |
| 3-37067 | 2/1991 | Japan . |
| 91/10417 | 7/1991 | World Int. Prop. O. . |

*Primary Examiner*—Randall L. Green
*Assistant Examiner*—P. Zuttarelli

[57] ABSTRACT

A fluid container comprises a drug container, a deformable solvent container, a double-pointed hollow needle having a sharp piercing edge at each end and being arranged between the drug container and the solvent container, a guide capsule with a cap rotatably mounted thereon, and a means for converting rotary motion of the cap to a linear motion of the drug container to push the drug container toward the solvent container in cooperation with the cap and the guide capsule so that a fluid communication is made between two containers through the needle.

22 Claims, 23 Drawing Sheets

FLUID CONTAINER

BACKGROUND OF THE INVENTION

1. Field of the Invention

The present invention relates to a fluid container and, more particularly, a fluid container capable of preserving a dry drug such as powdered drugs, freeze-dried drugs and sold preparations for example and a solvent in separated conditions and of aseptically mixing them just before use to administrate it as a liquid medicine to a patient.

2. Description of the Prior Art

In medical facilities such as hospitals, dry drugs in drug containers such as vials have been used for intravenous drip by dissolving them in a solvent such as distilled water, a physiological saline, a glucose solution, or a solution of an other drug solution dissolved therein.

In order to simplify such operations, there have been proposed various drug delivery systems designed such that a vial containing a dry drug is connected in series with a flexible container containing a solvent and adapted to be communicated with the latter just before use. Such drug delivery systems are disclosed, for example, in JP-T- S61-501129, JP-A- H 2-1277 and JP-A- S 63-135642, JP-T- S61-501129, which corresponds to U.S. Pat. No. 4,583,971, discloses a closed drug delivery system comprising a flexible container having a liquid diluent therein, a capsule coupled to the flexible container, a drug vial having a drug therein adapted to be mixed with the diluent, said drug vial being supported in the capsule by a supporting means of the capsule, and a coupling means for coupling the capsule to the interior of the flexible container. In this system, the drug vial is communicated with the flexible container by a communicating means arranged in the coupling means, thus making it possible to aseptically mix the drug with the solvent.

JP-A H2-1277, which corresponds to U.S. Pat. No. 4,936,841, discloses a fluid container comprising a flexible container containing a diluent, a capsule having a cylindrical connecting portion at its one end and being connected to a mouth of the flexible container at the connecting portion, a drug container held in the capsule, and a communicating member for communicating the flexible container with the drug container. In use, the communicating means is firstly pierced into the drug vial and then pierced into the flexible container to communicate the flexible container with the drug container. Since the flexible container is communicated with the drug container in the closed system, it is possible to aseptically mix the drug with the solvent.

JP-A S63-135642 (Japanese utility model application) discloses a drug delivery system comprising a solvent container containing a diluent therein, a drug container or vial containing a dry drug and arranged in series with the flexible container, and a double pointed hollow needle slidably supported by a ring removably arranged in the drug container, the hollow needle being adapted to be pierced at one end into a rubber stopper of the drug container and at the other end into a rubber plug of the flexible container to aseptically connect two container just before use.

All the above drug delivery systems of the prior art may be applied for various vials on the market. However, the drug delivery system of JP-T- S61-501129 requires a great number of different parts and makes it troublesome to open the passage between the vial and the diluent container as the opening of the passage is carried out by manually breaking a frangible member arranged between the vial and the diluent container. In addition, if the frangible member is broken defectively, a flow of the solvent is prevented because of a defective fracture of the frangible member, resulting in increase in a time for dissolving the drug in the solvent.

The drug delivery system of JP-A- H2-1277 has been improved in protection from contamination by foreign substances and in simplification of operations, as compared with that of JP-T- S61-501129. However, it also requires a great number of different parts and is complex in structure as the communicating member includes a controlling mechanism for controlling the order of fluid communication.

On the other hand, the drug delivery system of JP-A-S63-135642 is small in the number of parts and relatively easy to operate. However, it is required to apply a large external force to the system to communicate the vial with the liquid container. Further, it is required to remove the supporting ring and the double pointed needle from the solvent container after mixing the drug with the solvent to attach an infusion set to the plug of the solvent container. Thus, it is troublesome to handle. Also, there is a fear of leakage of the drug solution since the solvent container must be turned upside down after removal of the double pointed needle to insert an needle of the infusion set to the plug of the solvent container.

SUMMARY OF THE INVENTION

It is therefore an object of the present invention to provide a fluid container which is easy to operate, free from leakage of a drug solution and small in the number of parts, and makes it possible to aseptically mix a drug with a solvent.

Another object of the present invention is to provide a fluid container that can be classified easily into two or more kinds of parts by used material to perform treatment of classified refuse.

The above and other objects of the present invention are achieved by providing a fluid container comprising:

a drug container having a mouth sealed by a rubber stopper;

a deformable solvent container of a synthetic resin having at least one mouth sealed by a sealing means;

a double-pointed hollow needle having a sharp piercing edge at each end, said needle being arranged between the mouth of said drug container and that of the solvent container;

a guide capsule for slidably holding said double-pointed hollow needle and a part of said drug container, said guide capsule having an open end at one end and at the opposite end a connecting portion to be fitted on said mouth of the solvent container;

a cap rotatably mounted on said guide capsule to seal the open end of thereof, the greater part of said drug container being held in said cap; and a driving means for pushing said drug container toward said solvent container in cooperation with said cap and guide capsule, said driving means being so designed as to be driven by rotating said cap to force said drug container to move linearly toward said solvent container within the guide capsule without causing rotary motion thereof, thereby allowing said double-pointed hollow needle to pierce said rubber stopper of the drug container and said sealing means of the solvent container to make a fluid communication between said drug container and solvent container through said needle.

In use, the vial guide is moved linearly toward the solvent container by rotating the cap clockwise and the drug container held in the vial guide is forced to move toward the solvent container in straight motion without causing rotary motion. Thus, the rubber stopper of the drug container is pushed against and pierced by one end of the double-pointed needle and then the sealing means of the solvent container is pierced by the opposite end of the double-pointed needle. For this reason, a fluid communication is established between the drug container and solvent container through the double-pointed needle.

BRIEF DESCRIPTION OF THE DRAWINGS

The above and other objects and features of the present invention will become apparent from the following description taken in conjunction with the preferred embodiments thereof with reference to the accompanying drawings throughout which like parts are designated by like reference numerals, and in which.

DETAILED DESCRIPTION OF THE PREFERRED EMBODIMENTS

Figure 1:
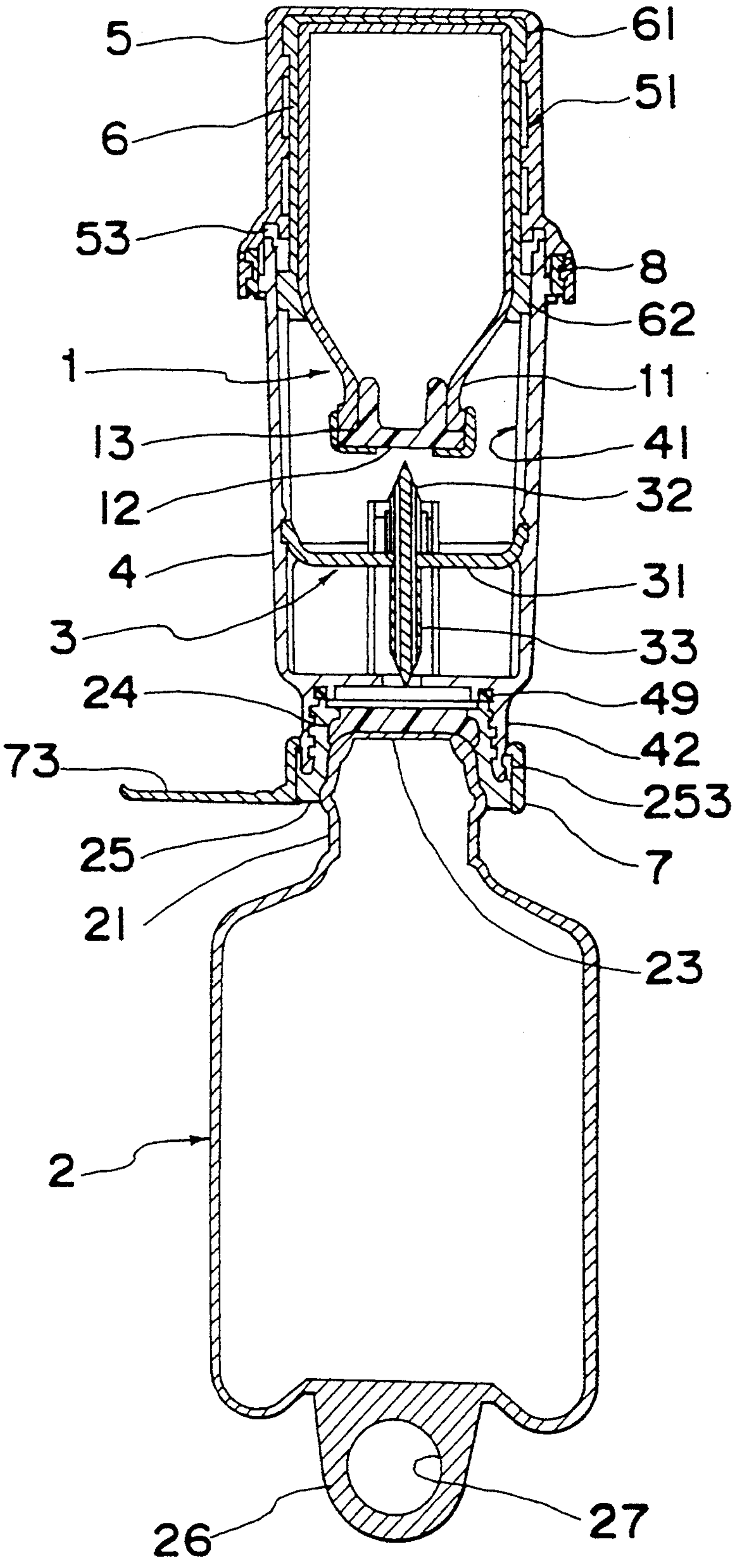
FIG. 1 is a schematic sectional view of a fluid container illustrating a preferred embodiment of the present invention.

Referring to FIG. 1, there is shown a fluid container according to the present invention, that comprises a drug container 1 such as vial; a solvent container 2; a double-pointed hollow needle 3 arranged between drug container 1 and solvent container 2 to make a fluid communication between them just before use; a cylindrical guide capsule 4 removably coupled to the solvent container 2 at one end thereof, said guide capsule 4 having an open end at one end and at the other end a connecting porion and aseptically holding the double-pointed hollow needle 3 in place; a cap 5 attached to the guide capsule 4 to close the open end thereof; and a vial guide 6 movably held in the cap 5, said vial guide 6 holding the drug container 1 in the reversed state and constituting a driving means for driving the drug container 1 toward the solvent container 2 in cooperation with both guide capsule 4 and cap 5.

The drug container 1 contains a dose of a dry drug such as powdered drugs, freeze-dried drugs and sold preparations, but such a dry drug is not illustrated in the drawings for the clarification of the figures. Similarly, the solvent container 2 contains a dose of a solvent or solution such as distilled water, a physiological saline, a glucose solution, or a solution of an other drug solution dissolved therein, but such a solvent is not illustrated in the drawings.

Figure 2:
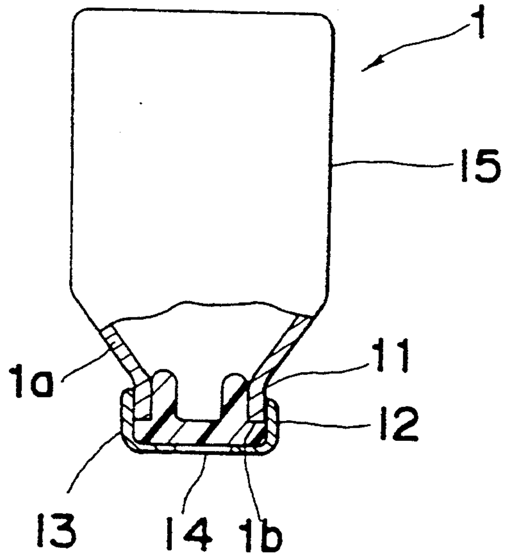
FIG. 2 is a partial cut-away side view of a drug container used in the fluid container of FIG. 1.

As best shown in FIG. 2, the drug container 1 is a small hollow vessel, usually of glass, having a mouth 11 sealed by a sealing means such as a rubber stopper 12. The rubber stopper 12 is fitted in the mouth 11 of the drug container 1 and fixed thereto by an aluminum covering member 13 secured on the mouth 11 of the drug container 1. As the drug container 1, there may be used those such as vials readily available on the market. The drug container 1 is held in the reversed condition in the vial guide 6, as shown in FIG. 1 and adapted to be moved downwardly by without causing rotary motion by the driving means. When the drug container 1 is to be assembled into the fluid container of FIG. 1, a closed top of the covering member 13 is partially removed from the drug container 1 to provide a hole 14 for insertion of the needle 3.

The solvent container 2 is a deformable vessel, usually of a relatively flexible resin such as polyethylene, polypropylene and polyesters, having a mouth 21 at one end and at the opposite end a closed bottom with a tab 26 serving as a hanging means.

Figure 4:
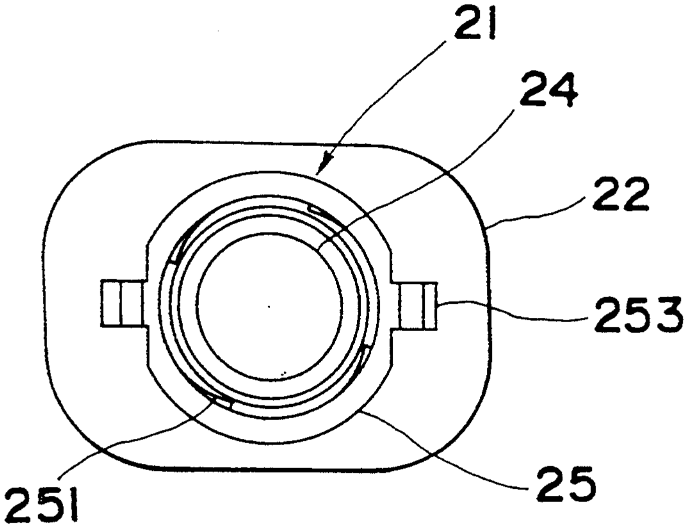
FIG. 4 is a top view of the solvent container of FIG. 3.
Figure 3:
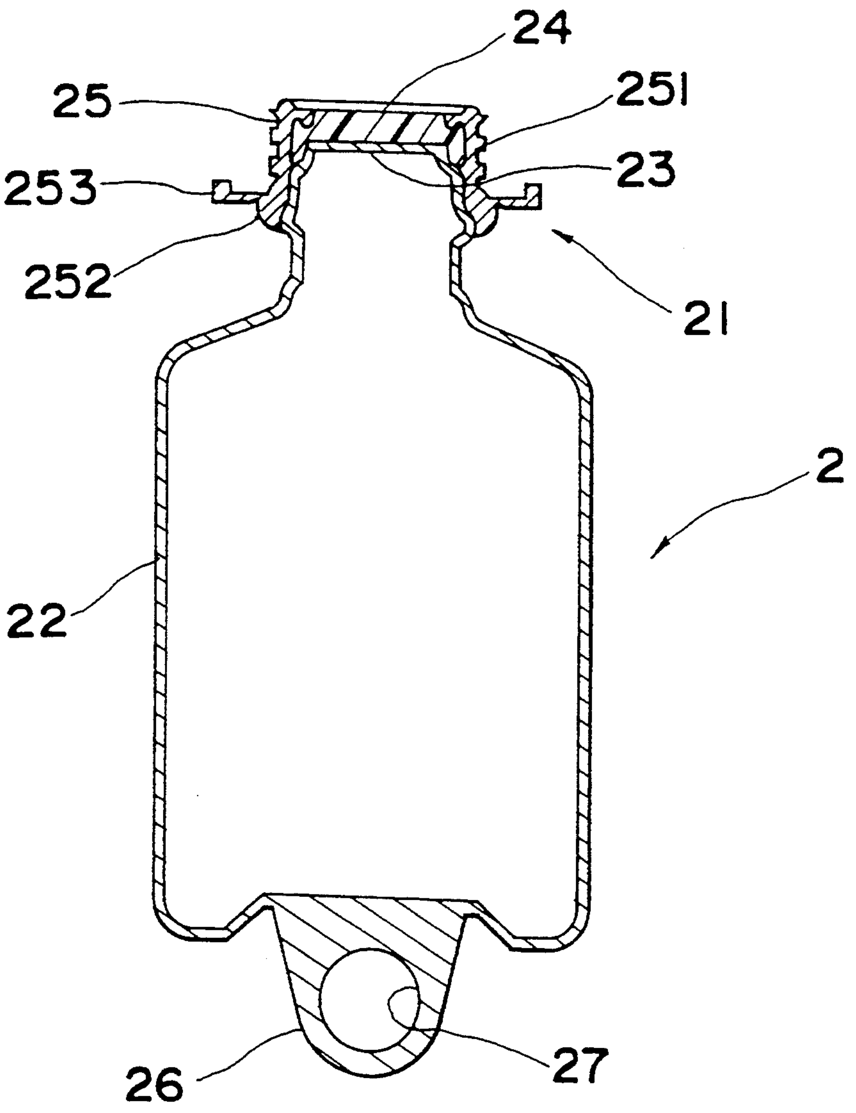
FIG. 3 is a sectional view of a solvent container used in the fluid container of FIG. 1.

As shown in FIGS. 3 and 4, the mouth 21 of the container 2 is sealed by a sealing membrane 23 integrally formed therewith and covered with a self-sealing means composed of a rubber stopper 24 and a covering member 25, like as the conventional bottles. The mouth 21 is adapted to be communicated with the drug container 1 through the double-pointed needle 3 and used as an outlet for the drug solution after removing the double-pointed needle 3 from the rubber stopper 24.

In this embodiment, the above rubber stopper 24 is attached to the mouth 21 of the solvent container 2 by placing it on the sealing membrane 23 and then fitting the covering member 25 on the mouth 21 of the solvent container 2. However, the attachment of the rubber stopper 24 may be carried out by preparing the covering member 25 with the rubber stopper 24 held therein, fitting the covering member 25 on the mouth of the container body 22, and then fixing the side wall 252 of the covering member 25 to the mouth 21 of the container body 22 by thermowelding.

The covering member 25 is provided on its side wall 252 with a male screw 251 adapted to be engaged with a female screw 421 of the connecting portion 42 of the guide capsule 4. Adjacent to the male screw 251, the covering member 25 has a pair of L-shaped fastening lobes 253 extending outwardly and diametrically from the lower end thereof. The fastening lobes 253 are fitted in stepped portions 43 of the guide capsule 4 and fixed by a lock ring 7 to prevent the guide capsule 4 from being out of place. Thus, when separating the guide capsule 4 from the solvent container 2, the fastening lobes 253 are taken off from the stepped portions 43 after removing the lock ring 7 and then the guide capsule 4 is turned clockwise or counterclockwise to loosen the screw.

The tab 26 is foldably jointed to the bottom of the solvent container 2 so that it is capable of being turned up and then hung on a hook or a hanger at its hole 27 after dissolution of the dry drug with the solvent.

The double-pointed hollow needle 3 is arranged between the drug container 1 and the solvent container 2 and held in the guide capsule 4. The double-pointed hollow needle 3 serves as a means for making a fluid communication between the drug container 1 and the solvent container 2. The needle 3 comprises a cannula 30 having a hub 31 attached to its middle part. The cannula 30 is a slender, pointed hollow member, usually of stainless steel or synthetic resin, having parallel two passages 35 extending therethrough and sharp edges at both ends. In case of taking a serious view of the sharpness of the needle, it is preferred to use stainless steel, preferably SUS 304 defined by JIS (corresponding to AISI 304), as a material for the cannula 30. On the other hand, in case of taking a serious view of problems in waste treatment and the mass-producibility of the needle, it is preferred to use plastics such as ABS resins, polycarbonates, high density polyethylene and the like.

Figure 5:
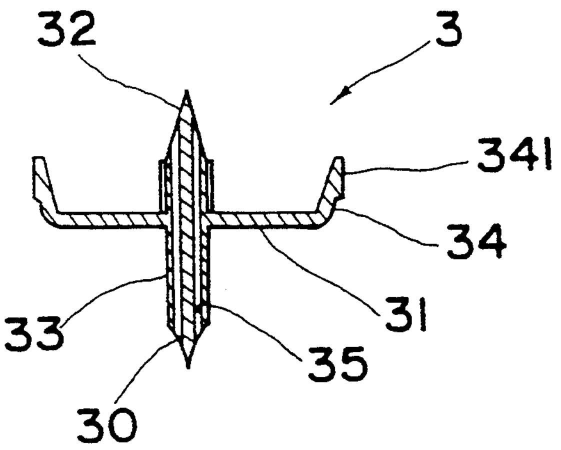
FIG. 5 is a sectional view of a double-pointed hollow needle used in the fluid container of FIG. 1.
Figure 6:
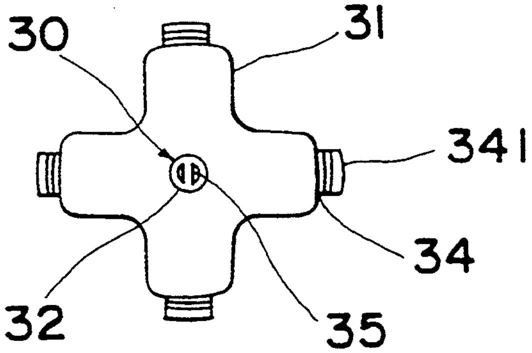
FIG. 6 is a top view of the needle of FIG. 5.

As best shown in FIGS. 5 and 6, the double-pointed hollow needle 3 has a hub 31 provided at a middle part of the needle, by which the hollow needle 3 is divided into two parts, i.e., an upper piercing needle 32 and a lower piercing needle 33. The hub 31 is usually of a resilient plastics in the form of a crossed piece having arms 34 which extend upwardly and outwardly from each free end of the crossed piece. The arms 34 are provided at their free ends with a small, outwardly protruded portion 341 adapted to be rested on stepped portions 441 in needle guide grooves 44 of the guide capsule 6 to hold the needle 3 in place. The arms 34 may be designed such that the protruded portions 341 are allowed to be disengaged from the stepped portions 441 only when a load applied to the needle 3 by the drug container 1 exceeds a predetermined value which may be determined by the size and material of the arms.

The upper piercing needle 32 may be so designed as to have an edge sharper than that of the lower piercing needle 33 to ensure that the upper piercing needle 32 is pierced into the rubber stopper 12 of the drug container 1 first and then the lower piercing needle 33 is pierced into the rubber stopper 24 of the solvent container 2.

Figure 7:
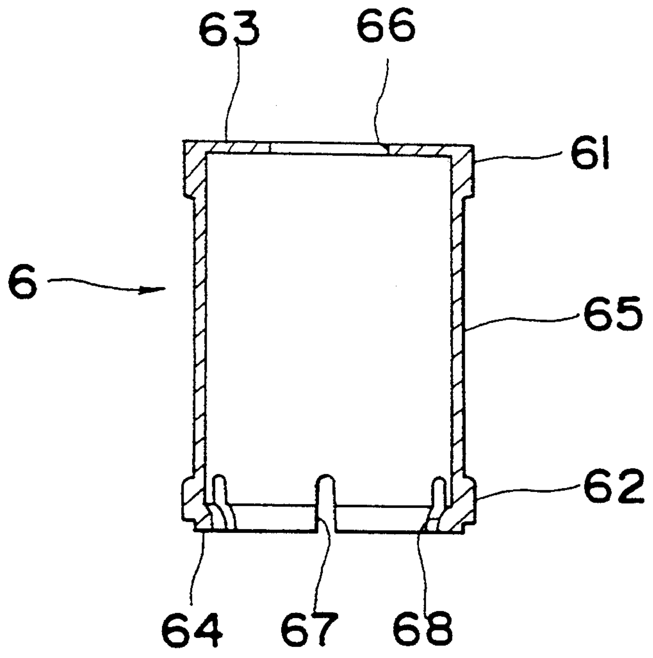
FIG. 7 is a sectional view of a vial guide used in the fluid container of FIG. 1.
Figure 8:
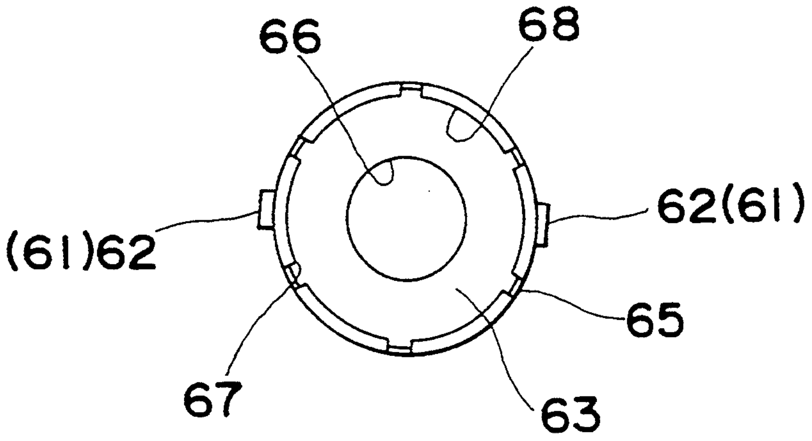
FIG. 8 is a bottom view of the vial guide of FIG. 7.

As shown in FIGS. 7 and 8, the vial guide 6 is a partially top-closed cylindrical hollow member, usually of a synthetic resin such as polyethylene, polypropylene, polyesters, polyvinyl chlorides, polycarbonates and ABS resins, having a top 63 and a mouth 64. The vial guide 6 constitutes a driving means for converting a rotary motion of the cap 5 to a linear motion of said drug container 1 in cooperation with the cap 5 and guide capsule 6.

A barrel 65 of the vial guide 6 is provided at its upper part close to the top 63 with first projections 61, in this embodiment two projections, for engagement with spiral grooves 51 of the cap 5 mentioned later. The barrel 65 is also provided, at its lower part close to the mouth 64, with second projections 62, in this embodiment two projections, for engagement with vertical guide grooves 41 of the guide capsule 4 mentioned later. Each second projection 62 is positioned on a line extending in parallel with the axis of the barrel 65.

The vial guide 6 is provided at its top wall 63 with a hole 66 to allow the air present in the barrel 65 to escape therethrough during insertion of the drug container 1 into the vial guide 6. The mouth 64 of the vial guide 6 is tapered and divided into several parts together with a lower part of the barrel 65 by several slits 67, and the drug container 1 is held in the vial guide 6 and prevented from falling off by projections 68 on the lower side of the vial guide 6. The vial guide 6 with the drug container 1 is partially located in the guide capsule 4.

Figure 9:
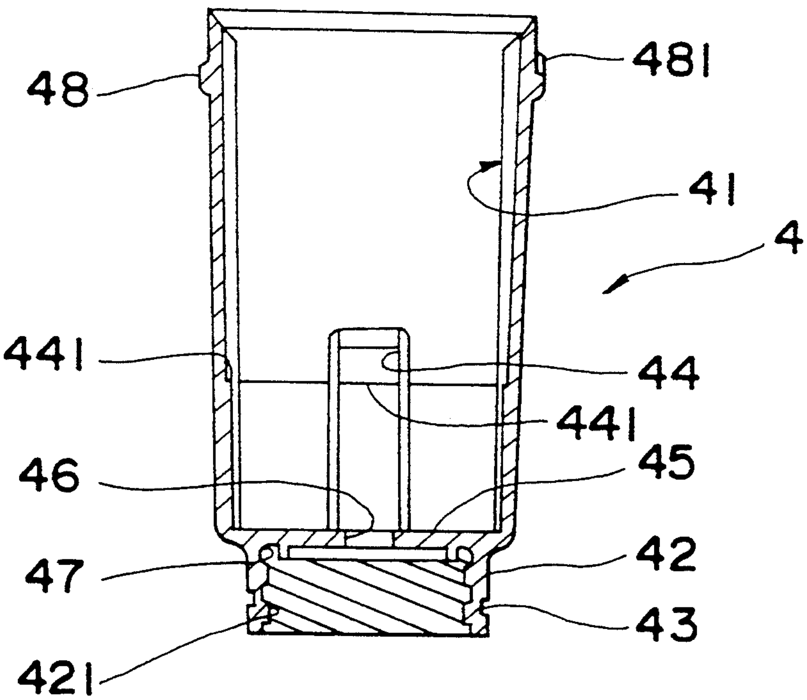
FIG. 9 is a sectional view of a guide capsule used in the fluid container of FIG. 1.
Figure 10:
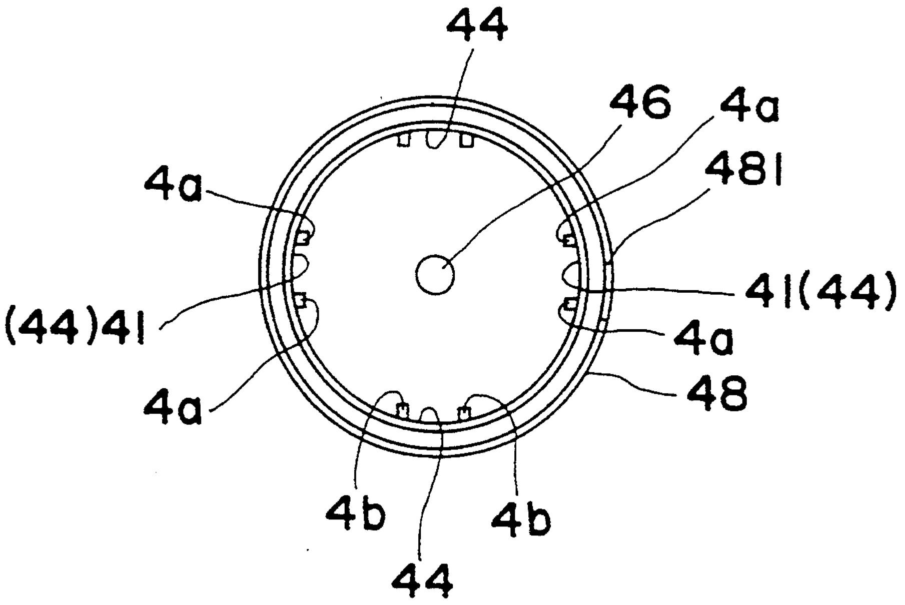
FIG. 10 is a top view of the guide capsule of FIG. 9.

As shown in FIG. 9 and 10, the guide capsule 4 is a cylindrical hollow member, usually of a synthetic resin similar to that of the vial guide, having an open end and a small-sized connecting portion 42 reduced in diameter and partitioned from the upper part by a partition wall 45.

The guide capsule 4 has several pairs of vertical projections 4*a* and 4*b* integrally formed on its inner wall in parallel with the axis of the guide capsule 4. Two pairs of the diametrically arranged vertical projections 4*a* extend from the partition wall 45 toward the open end of the guide capsule 4 and terminates at the position close to the open end of the guide capsule 4 to form guide grooves 41, while the remaining two pairs of the diametrically arranged projections 4*b* extend from the partition wall 45 toward the open end of the guide capsule 4 and terminate at a middle part of the guide capsule 4 to form needle guide grooves 44.

The needle guide grooves 44 serve as guide grooves for the arms 34 of the double-pointed hollow needle 3 which has four arms 34 in this embodiment. On the other hand, the guide grooves 41 serve both as guide grooves for the second projections 62 of the vial guide 6 and as guide grooves for the double-pointed hollow needle 3 so that the vial guide 6 and the needle 3 are moved downwardly without causing rotary motion. The grooves 41 are reduced in depth at their middle portion to form stepped portions 441 to hold the double-pointed hollow needle 3 in place. Such stepped portions 441 are also provided at the upper part of the grooves 44.

Close to the open end of the guide capsule 4, there are provided an annular projection 48 for attachment of the cap 5, and projections 481 adapted to be engaged with locking projections 85 of a cap-release member 8 to prevent the cap-release member 8 from rotation counterclockwise. In the inner wall of the connecting portion 42 adjacent to the partition wall 45 of the guide capsule 4, there is provided an annular groove 47 for attachment of a sealing member 49.

The partition wall 45 of the guide capsule 4 is provided with a through hole 46 around the axis of the guide capsule 4, through which the lower piercing needle 33 of the double-pointed needle 3 is pierced into the rubber stopper 24. The gap between the guide capsule 4 and the solvent container 2 is sealed tightly to prevent flow of fluid by the sealing member 49 arranged in an annular groove 47.

The connecting portion 42 of the guide capsule 4 is provided with a female screw 421 for engagement with the solvent container 2, that is engaged with a male screw 251 provided on the mouth 21 of the solvent container 2. At a lower part of the connecting portion 42 there are provided two stepped portions 43 adapted to be engaged with fastening lobes 253 of the solvent container 2. Thus, the guide capsule 4 is so designed that it is incapable of being removed from the solvent container 2 except on condition that the fastening lobes 253 of the solvent container 2 are disengaged from the stepped portions 43 of the guide capsule 4. The fastening lobes 253 are fixed in place by a lock ring 7 for guide capsule, mentioned later in connection with FIG. 14, so that they are not displaced from the stepped portions 43.

The guide capsule 4 is removably coupled to the mouth 21 of the solvent container 2 at a connecting portion 42 thereof by the lock ring 7 and at the opposite end sealed by the cap 5.

The cap 5 serves both as a hermetic sealing means for the guide capsule 4 and as a means for driving the drug container 1 downwardly in cooperation with the vial guide 6 and guide capsule 4.

Figure 11:
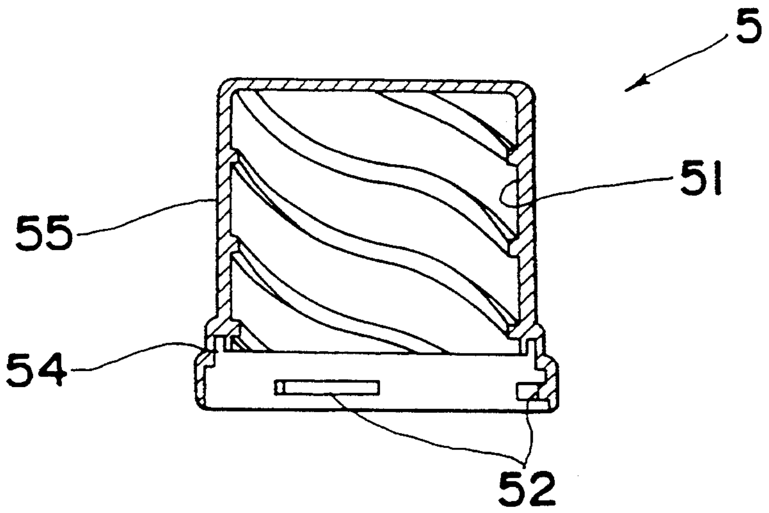
FIG. 11 is a sectional view of a cap used in the fluid container of FIG. 1.
Figure 12:
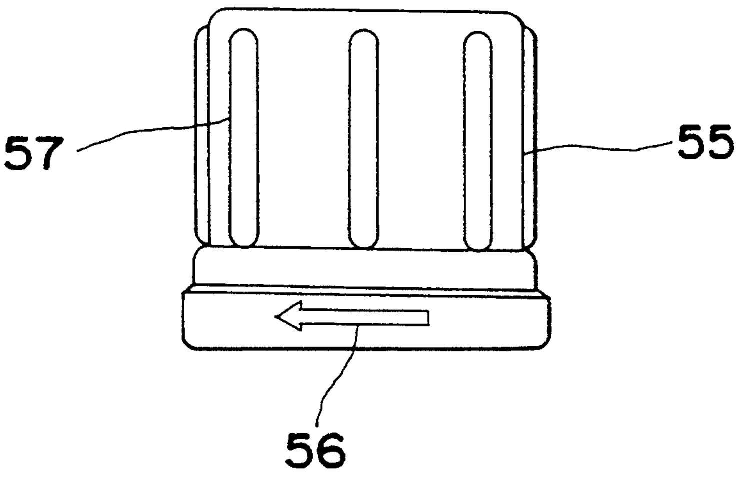
FIG. 12 is a side view of the cap of FIG. 11.
Figure 13:
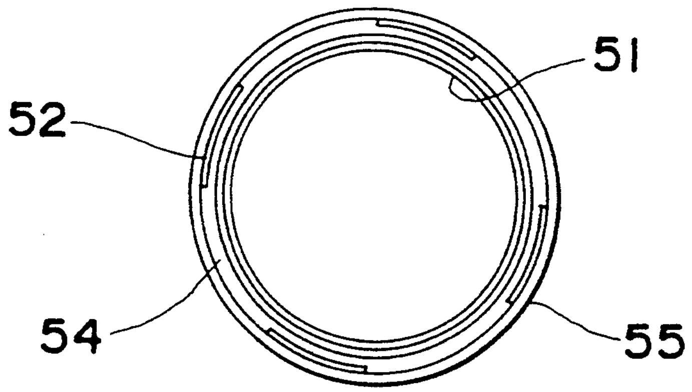
FIG. 13 is a bottom view of the cap of FIG. 11.

As shown in FIGS. 11 to 13, the cap 5 is a top-closed cylindrical hollow member, usually of a synthetic resin similar to that of the guide capsule 4. The cap 5 is provided at its free end, i.e., lower part of a skirt 55 thereof, with an annular groove 54 in which a sealing member 53 is fitted to form a hermetic seal between the cap 5 and the guide capsule 4.

In the inner wall of the skirt 55 of the cap 5 there are provided two spiral grooves 51 adapted to be engaged with the respective first projections 61 of the vial guide 6. If the cap-release member 8 is used to removably attach the cap 5 to the guide capsule 4, the cap 5 is provided on a lower part of the inner wall of its skirt 55 with projections 52 adapted to be fitted in grooves 82 of the cap-release member 8.

The spiral grooves 51 run spirally along the inner wall of the cap 5 from the top to the lower end. The spiral grooves 51 form a means for driving the drug container 1 downwardly together with the first and second projections 61 and 62 of the vial guide 6 and the vertical guide grooves 41 of the guide capsule 4. Instead of the spiral grooves 51, there may be used spiral projections formed on the inner wall of the cap 5. In this case, the first projections 61 of the vial guide 6 are so arranged that each projection 61 comes in contact with the lower side of the spiral projection.

The above fluid container may be assembled by hermetically and removably fitting the guide capsule 4 on the solvent container 2, fitting the lock ring 7 on the connecting portion 42 of the guide capsule 4, placing the double-pointed hollow needle 3 in the guide capsule 4, and hermetically fitting the cap 5 with drug container 1 on the open end of the guide capsule 4. In this case, it is possible to use the cap-release member 8 to removably couple the guide capsule 4 and the cap 5.

Figure 14:
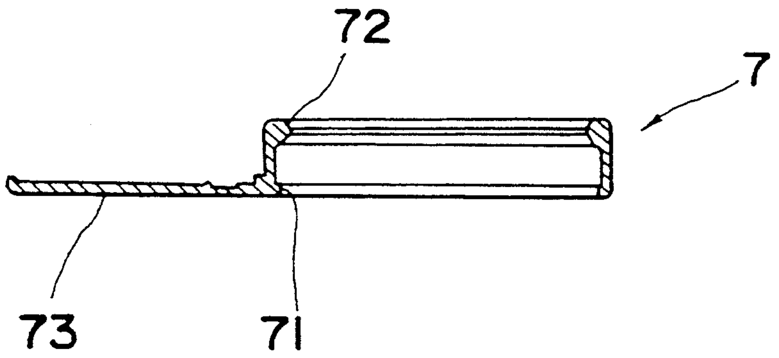
FIG. 14 is a sectional side view of a lock ring used in the fluid container of FIG. 1.
Figure 15:
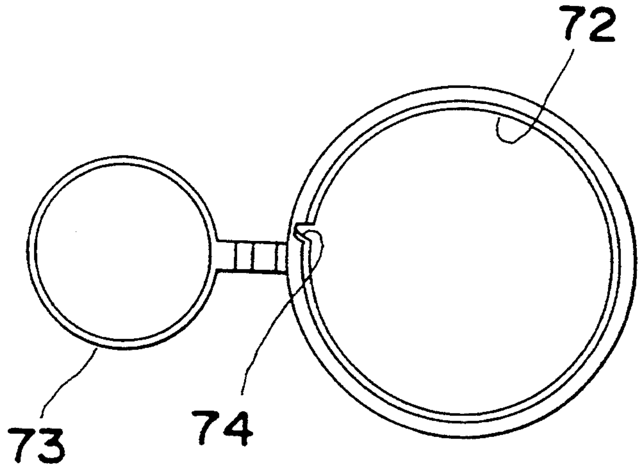
FIG. 15 is a top view of the lock ring of FIG. 14.

The lock ring 7 has been provided to avoid accidental disengagement of the guide capsule 4 from the solvent container 2. As shown in FIGS. 14 and 15, the lock ring 7 has first and second annular projections 71 and 72 and a pulling tab 73 integrally formed therewith. The first projections 71 is adapted to be engaged with the covering member 25 fitted on the mouth of the solvent container 2, while the second projection 72 is adapted to be engaged with the upper end of the fastening lobes 253 engaged with the stepped portion 43 of the guide capsule 4. Also, the ring 7 is provided with a weakened part 74 to make it breakable.

When removing the guide capsule 4 from the solvent container 2, the ring 7 is removed by pulling the pulling tab 73 until the weakened part 74 is broken, disconnecting the fastening lobes 253 from the stepped portions 43 of the guide capsule 4, and then turning the guide capsule 4 in the direction of loosening the screw.

Figure 16:
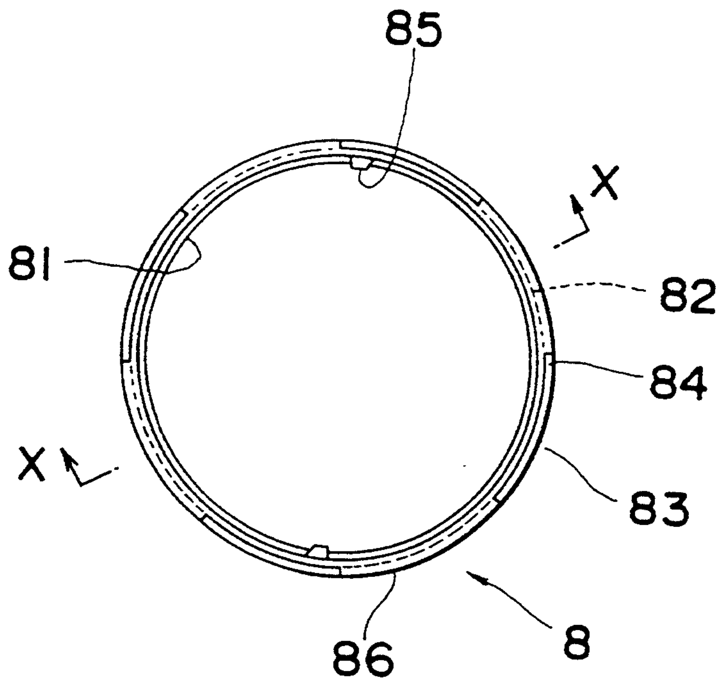
FIG. 16 is a top view of a cap-release member used in the fluid container of FIG. 1.
Figure 17:
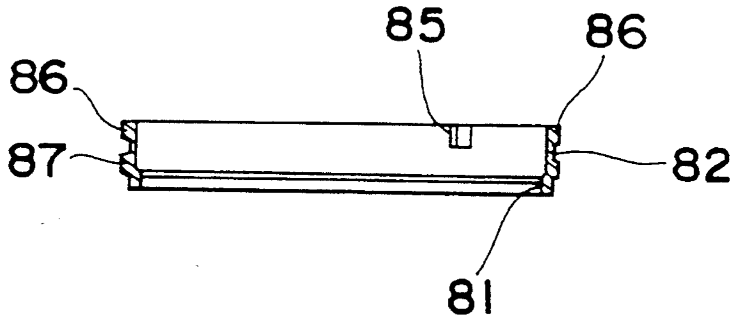
FIG. 17 is a sectional view of the cap-release member taken along a line x—x in FIG. 16.

The cap-release member 8 is used to make it possible to perform classified treatments of waste parts such as, for example, drug container 1 and double-pointed hollow needle 3 of the fluid container after use. As shown in FIGS. 16 and 17, the cap-release member 8 is a ring-like member, usually of synthetic resins, having an annular rib 81 formed on an inner wall thereof and an annular groove 82 formed in an outer wall thereof. The annular rib 81 is rotatably engaged with the annular projection 48 of the guide capsule 4, while the annular groove 82 is engaged with the projection 52 of the cap 5.

An upper flange or wall of the cap-release member 8 that constitutes a side of the annular groove 82 is partially cut out at several parts to form arched cuts 83 and arched rims 86. The arched cuts 83 have a length greater than that of the projections 52 of the cap 5. Between the arched cut 83 and the arched rim 86, there is provided a locking projection 84. When the cap 5 is rotated clockwise, the projection 52 of the cap 5 comes into collision with one side of the projection 84 and allows the cap-release member 8 to rotate with the cap 5. In this case, the projection 52 is positioned between the arched rim 86 and the lower flange or wall 87 of the cap-release member 8. On the other hand, when the cap 5 is rotated counterclockwise, the projection 52 of the cap comes into contact with the opposite side of the projection 84 and is positioned below the arched cut 83.

Thus, the cap 5 can be removed from the cap-release member 8 by pulling it upwardly as the projections 52 of the cap 5 are designed so as to have a length smaller than that of the arched cut 83.

Since the cap-release member 8 is entirely hidden by the lower part of the skirt 55, it is impossible to rotate the cap-release member 8 alone by hand. In order to prevent the cap-release member 8 from rotation along with the cap 5 when removing the cap, the cap-release member 8 is provided with a projection 85 on an upper part of the inner wall of the cap-release member 8 so that the projection 85 is engaged with projection 481 formed on the upper part of the outer wall of the guide capsule 4. Further, the projection 85 is so designed that the projection 481 of the guide capsule 4 can pass over the projection 85 when rotating the cap 5 clockwise to make a fluid communication between the drug container 1 and the solvent container 2.

The fluid container of the present invention is operated, for example, in the following manner.

Firstly, the cap 5 is rotated clockwise. This rotary motion of the cap 5 is converted to a linear motion of the vial guide 6 as the vial guide 6 is engaged at its first projections 61 with the spiral grooves 51 of the guide capsule 4 and prevented from its rotary motion by its second projections 62 engaged with the vertical guide grooves 41 of the guide capsule 4. Thus, the drug container 1 held in the vial guide 6 is moved downwardly along the guide grooves 41 of the guide capsule 4 without causing rotary motion.

During downward movement of the vial guide 6, the rubber stopper 12 fitted in the mouth 11 of the drug container 1 is pierced by the upper piercing needle 32 of the double-pointed needle 3, while the rubber stopper 24 and sealing membrane 23 of the solvent container 2 are pierced by the lower piercing needle 33 of the double-pointed needle 3. Thus, a fluid communication is made between the drug container 1 and solvent container 2 through the double-pointed hollow needle 3.

Then, the drug in the drug container 1 is mixed with the solvent in the solvent container 2 in the following manner. Firstly, the fluid container is turned upside down, thereby allowing the solvent to flow into the drug container 1 where the solvent is mixed with the dry drug. If necessary, the solvent container 2 is pressed and deformed by hand to accelerate flow of the solvent. Then, the fluid container is turned upside down again so that the resultant drug solution in the drug container 1 is returned to the solvent container 2. If the drug container 1 has been deformed, the flow of the drug solution is accelerated by a pumping action of the solvent container 2 since the pressed solvent container 2 is restored to its original state by its elasticity.

After removing the lock ring 7 from the guide capsule 4 and then releasing the fastening lobes 253 from the stepped portions 43 of the guide capsule 4, the guide capsule 4 is then unscrewed by turning and then removed from the solvent container 2. Then, the solvent container 2 is hanged at its tab 26 on a hanger (not shown) and then connected to an infusion set by piercing a needle of the infusion set into the rubber stopper 24 on the mouth 21 of the solvent container 2.

When the fluid container is to be disposed after use, the used fluid container can be classified into two or more kinds of parts by material used, thus making it possible to perform treatment of classified waste. In this case, the cap 5 is removed from the cap-release member 8 by turning it counterclockwise, and then the drug container 1 and the double-pointed needle 3 are taken out from the guide capsule 4 with ease.

In the above embodiment, there has been used the double-pointed hollow needle 3 in the form of a small, slender hollow member having a tapered, sharp edges at either ends. However, it is possible to use a double-pointed hollow needle having any desired configuration of piercing edges as occasion demands.

Further, the double-pointed hollow needle 3 of FIG. 1 is provided with two passages 35 to allow the solvent to flow into the drug container 1 without causing deformation of the solvent container, but it is also possible to use a double-pointed hollow needle with one passage 35. In this case, it is required to deform the solvent container by applying compressive stresses to the solvent container to allow the solvent to flow into the drug container 1.

Figure 18:
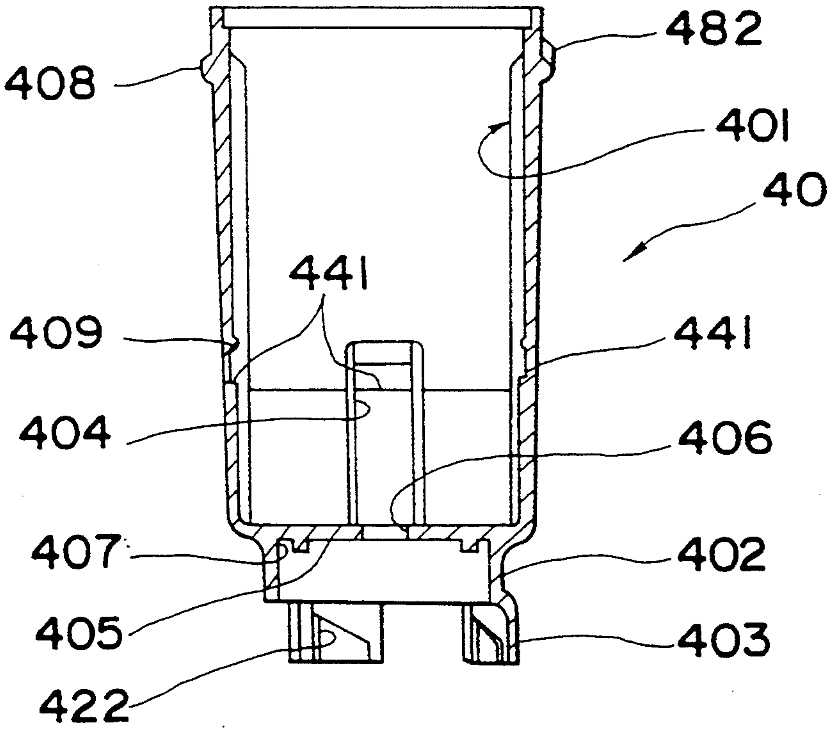
FIG. 18 is a sectional view of a guide capsule showing another preferred embodiment of the present invention.
Figure 19:
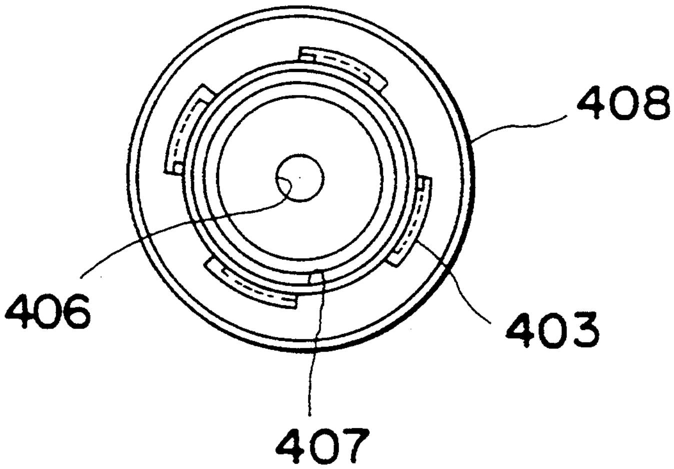
FIG. 19 is a bottom view of the guide capsule of FIG. 18.

The guide capsule 4 may be modified as shown in FIGS. 18 and 19. In this embodiment, a guide capsule 40 is provided with vertical guide grooves 401, a connecting portion 402, coupling legs 403 having a configuration formed complimentarily with a configuration of the coupling projections 20 formed on the mouth 201 of a solvent container 202 shown in FIG. 22, needle guide grooves 404, a partition wall 405, a through hole 406, an annular groove 407 for a sealing member such as 0-ring (not shown), an annular projection 408, a stop rib 409 for prevent the double pointed needle 3 from upward movement, a recess 422 for preventing the guide capsule 40 from rotation in the direction which loosens the coupling between the guide capsule 40 and solvent container 20, stepped portions 441, and projections 482 for preventing the cap-release member 8 from a counterclockwise rotation.

The needle guide grooves 44 or 404 may be substituted with the guide grooves 41 or 401. Also, the guide capsule 4 or 40 may have only two grooves individually provided in the inner wall thereof. If the guide grooves 41 or 401 are not used as guide grooves for the double-pointed hollow needle 3, they may be terminated at the stepped portions 441 as there is no need to provide a part extending from the stepped portion 441 to the partition wall 45 or 405.

The cap-release member 8 may be omitted from the fluid container. In this case, it is unnecessary to provide the annular projection 48, provided that the cap 5 is rotatably mounted on the guide capsule 4 by providing complementary undercuts both in the guide capsule 4 and the cap 5.

Figure 22:
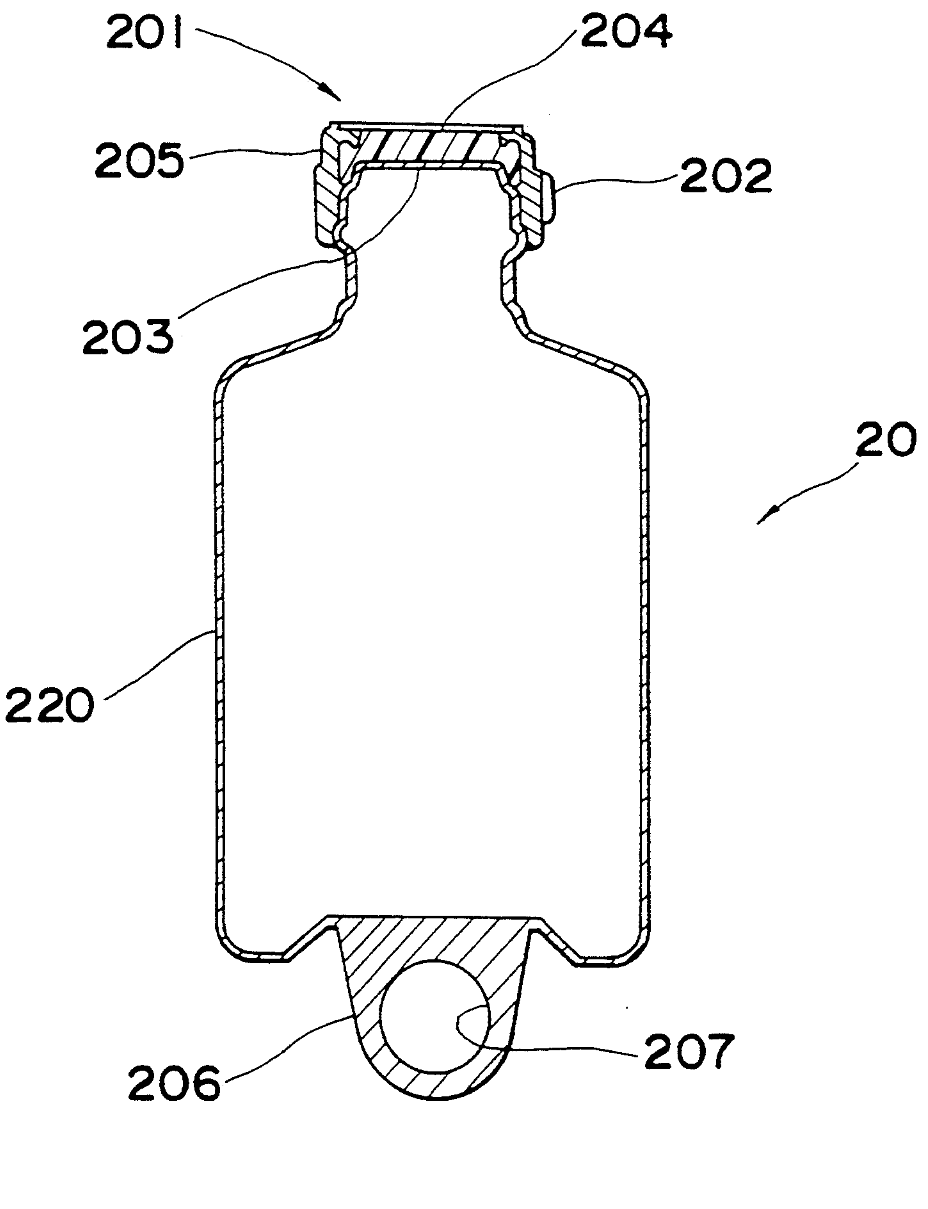
FIG. 22 is a sectional view of a solvent container illustrating another embodiment of the present invention.
Figure 23:
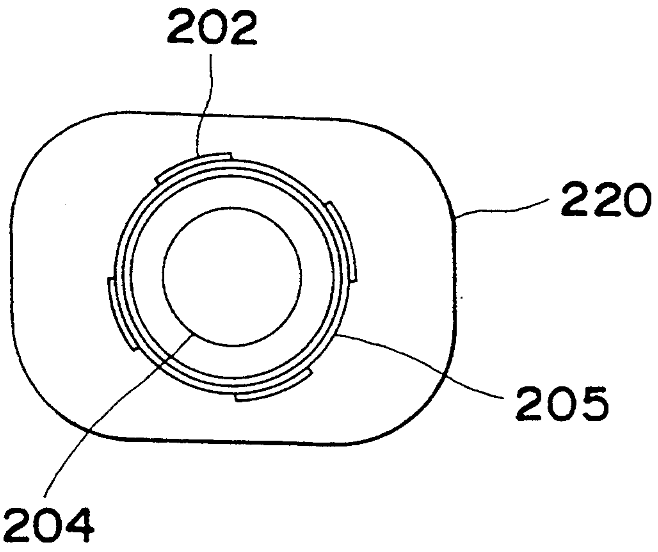
FIG. 23 is a top view of the solvent container of FIG. 22.
Figure 24:
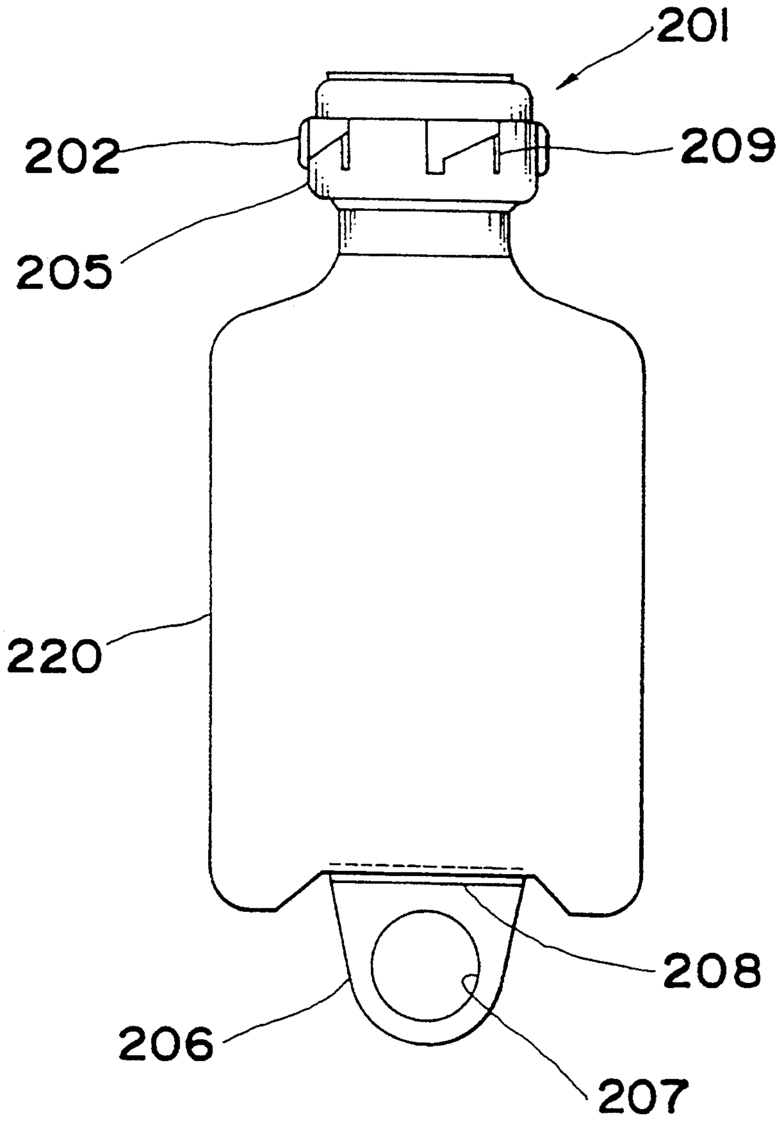
FIG. 24 is a front view of the solvent container of FIG. 22.

The solvent container 2 may be modified as shown in FIGS. 22 to 24, in which reference numeral 201 is a mouth, 202 a coupling projection having a configuration complementary with a coupling leg 403 of the guide capsule 40, 203 a sealing membrane, 204 a rubber stopper, 205 a covering member, 206 a tab, 207 a hole, 208 a hinged portion, 209 projections adapted to be fitted in recesses 422 of the guide capsule 40 to prevent it from rotary motion.

The vial guide 6 may be omitted from the fluid container as occasion demands. In this case, projections corresponding to first and second projections 61 and 62 of the vial guide 6 of FIG. 1 are provided on the barrel 15 of the drug container 1 to constitute the driving means for converting the rotary motion of the cap 5 to the linear motion of the drug container 1 in combination with the guide capsule 4 and the cap 5. However, it is preferred to use a vial guide 6 made of a synthetic resin to hold the drug container 1 therein since it is difficult with glass to produce drug containers having projections corresponding to first and second projections 61 and 62.

Further, the drug-container driving means may be constituted by using a cap having projections corresponding to the projections 61 of the vial guide 6 in combination with a vial guide having second projections 62 and spiral grooves corresponding to the spiral grooves 51 of the cap 5. It is also possible to use a vial guide provided with first projections 61 and vertical grooves corresponding to the grooves 41 of the guide capsule 4, in combination with a guide capsule provided with the second projections corresponding to the second projections 62 of the vial guide 6, and the cap 5 provided with spiral grooves 61. In FIG. 12, an arrow 56 indicates a rotary direction of cap 5, and 57 are ribs for preventing it from a slippage.

In the above embodiment, the spiral grooves 51 and vertical guide grooves 41 are formed by a pair of projections which are respectively provided on the walls of the cap 5 and guide capsule 4. However, the spiral grooves 51 and vertical guide grooves 41 are never limited to the above example only and they may be provided in the walls of the cap 5 and guide capsule 4, respectively.

In the above embodiment, the cap 5 and guide capsule 4 are coupled by means of the cap-release member 8 such that the arched projections 52 are fitted in the annular arched grooves 82. It is also possible to use any other coupling means such as screw coupling, lure coupling and the like, provided that it allows the cap-release member 8 to run idle when rotating the cap 5 clockwise, but allows the cap-release member 8 to rotate together with the cap 5 when rotating the cap 5 counterclockwise so that the cap 5 can be removed from the guide capsule 4.

Figure 20:
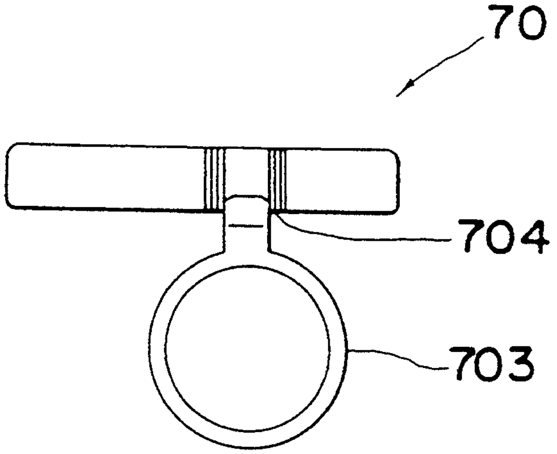
FIG. 20 is a side view illustrating another form of a lock ring used in the present invention.
Figure 21:
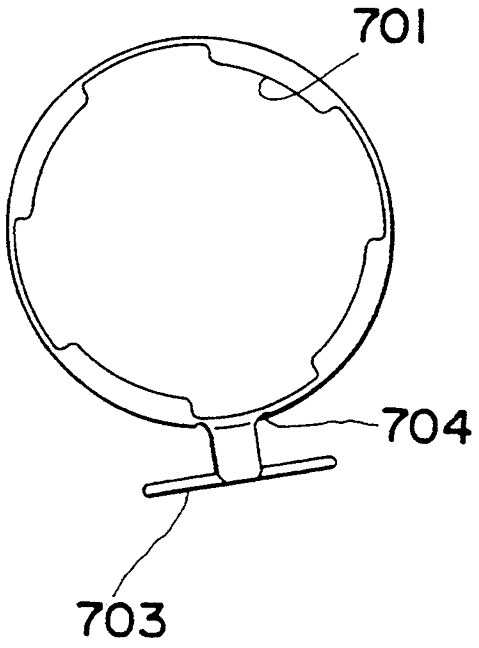
FIG. 21 is a top view of the lock-ring of FIG. 20.

The lock ring 7 may be replaced with a lock ring 70 having a configuration as shown in FIGS. 20 and 21. The lock ring 70 is used to fix the guide capsule 40 shown in FIG. 18 to the mouth 201 of the solvent container 20 shown in FIG. 22. In FIGS. 20 and 21, numeral 701 indicates projections adapted to be fitted in recesses formed between the guide capsule 40 solvent container 20 by connecting the coupling legs 403 of the guide capsule 40 to the coupling projections 202 of the solvent container 20. The projections 701 prevent the guide capsule 40 and the solvent container 20 from relative rotary motion. Numeral 703 is a pulling tab and 704 is a weakened part.

In the embodiment of FIGS. 16 and 17, a mechanism for removal of the cap 5 is constituted by the annular groove 82, arched cuts 83 and locking projections 84, all of which are provided on the outside of the cap-release member 8. However, such a mechanism may be provided on the inside of the cap-release member 8 and may be used in combination with a projection formed on the lower part of the outer wall of the skirt 55 of the cap 5 so as to have a configuration corresponding to that of the projection 52. In this case, the cap 5 can not be rotated counterclockwise before use as the spiral grooves 51 are engaged with the first projections 61 of the vial guide 6, but the cap 5 can be removed even before use by only rotating the cap-release member 8 counterclockwise. It is therefore necessary to provide any means for preventing the cap 5 from being removed before use.

As can be seen from the above, according to the present invention, it is possible to provide a fluid container which is simple in construction and easy to handle, and enables to aseptically mix the drug with the solvent. Further, it is possible to provide a fluid container at a moderate price as it requires small number of parts. In addition, the provision of the cap-release member makes it possible to perform classified treatment of waste. In addition, there is no fear of leakage of the drug solution from the fluid container.

Figure 25:
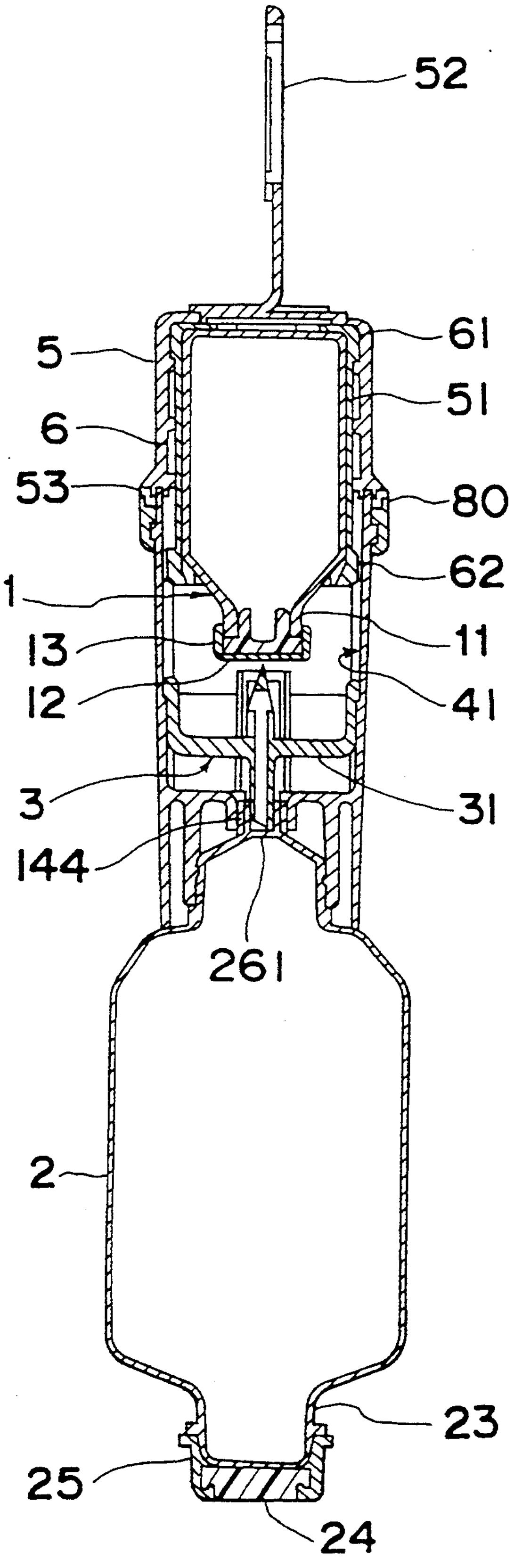
FIG. 25 is a schematic sectional view of a fluid container illustrating another preferred embodiment of the present invention.

Referring now to FIG. 25, there is shown another preferred embodiment of a fluid container of the invention. The fluid container comprises a vial or drug container 1 containing a dry drug (not shown), a solvent container 2 containing a solvent or a solution (not shown), a double-pointed hollow needle 3, a guide capsule 4 removably coupled to the solvent container 2 at one end thereof, a cap 5 attached to the guide capsule 4 to close the opposite open end thereof, and a vial guide 6 arranged in the cap 5. The drug container 1 is held in the vial guide 6 in the reversed state so that a neck and a mouth 11 thereof are protruded beyond the lower end of the vial guide 6. The vial guide 6 constitutes a driving means for forcing the drug container 1 to move toward the solvent container 2 in cooperation with the guide capsule 4 and cap 5. If the cap 5 is rotated by hand, the vial guide 6 movably held therein is forced to move toward the solvent container 2 along with the drug container 1 held therein. During movement of the drug container 1, the rubber stopper 12 of the drug container 1 is pierced by one pointed end of the double-pointed hollow needle 3, while the sealing membrane 23 of the solvent container 2 is pierced by the opposite end of the needle 3. Thus, a fluid communication is established between the drug container 1 and the solvent container 2 though the double-pointed hollow needle 3.

The drug container 1 is a small hollow vessel, usually of glass, having a neck and a narrow mouth 11 sealed by a rubber stopper 12. Since the drug container 1 has the same structure as that of the drug container employed in the embodiment of FIG. 1, there would be no need to explain the drug container 1 repeatedly.

Figure 26:
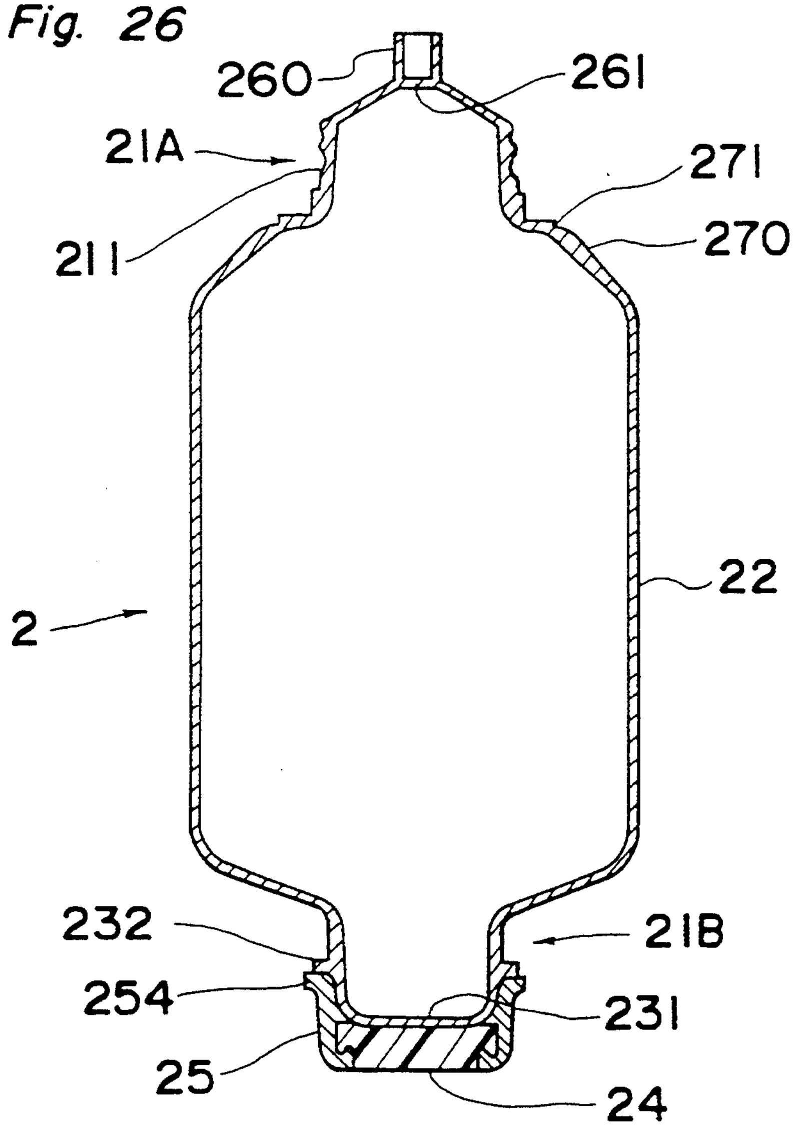
FIG. 26 is a sectional view of a solvent container used in the fluid container of FIG. 25.

As best shown in FIG. 26, the solvent container 2 is a deformable vessel, usually of a relatively flexible synthetic resin, having a narrow mouth 21A, 21B at each end of a container body 22. One of the mouths, an upper mouth 21A in FIG. 26, is used as a portion to be communicated with the drug container 1 by the double-pointed hollow needle 3, while the other mouth, a lower mouth 21A is used as an outlet for drug solution.

The upper mouth 21A is tapered and then continued straight up to the top to form a tubular needle guide 260, and closed at a tapered tip or a bottom of the tubular needle guide 260 by a sealing part 261 formed integral with the solvent container 2. The upper mouth 21A is provided in its outer wall with a male screw 211 adapted to be engaged with the female screw 421 of the guide capsule 4, the part below swelling out to form a shoulder 270 and then continuing straight down to the lower end of the container body 22.

The lower part of the solvent container 2 tapers and then continues straight down to the lower end to form the lower mouth 21B with a flange 232. The lower mouth 21 is closed by a sealing membrane 23 integrally formed therewith and covered with a self-sealing means composed of a rubber stopper 24 and a covering member 25. The covering member 25 is fixed at its flange 254 to the flange 232 of the lower mouth 21B by thermowelding. If necessary, the rubber stopper 24 may be covered with a thin plastic film to prevent its surface from contamination.

The upper mouth 21A of the solvent container 2 is never limited to the above configuration having the bottom-closed needle guide 260. It may take any configurations as occasion demands. For example, the upper mouth 21A may take the same configuration as that of the lower mouth 21B closed by a sealing membrane 23 integrally formed therewith and covered with a self-sealing means composed of a rubber stopper 24 and a covering member 25.

Figure 27:
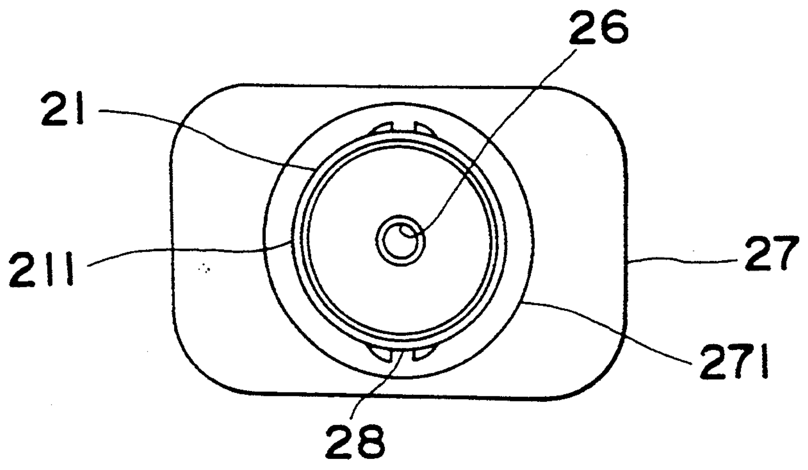
FIG. 27 is a top view of the solvent container of FIG. 26.

At an upper part of the shoulder 270, there is provided an annular stepped portion 271 on which the guide capsule 4 is fitted. However, it is not necessarily required to provide the stepped portion 271. Further, if necessary, there may be provided grooves 28 for engagement with projections 143 of the guide capsule 4 on the outer wall of the mouth 21A, as shown in FIG. 27.

Figure 28:
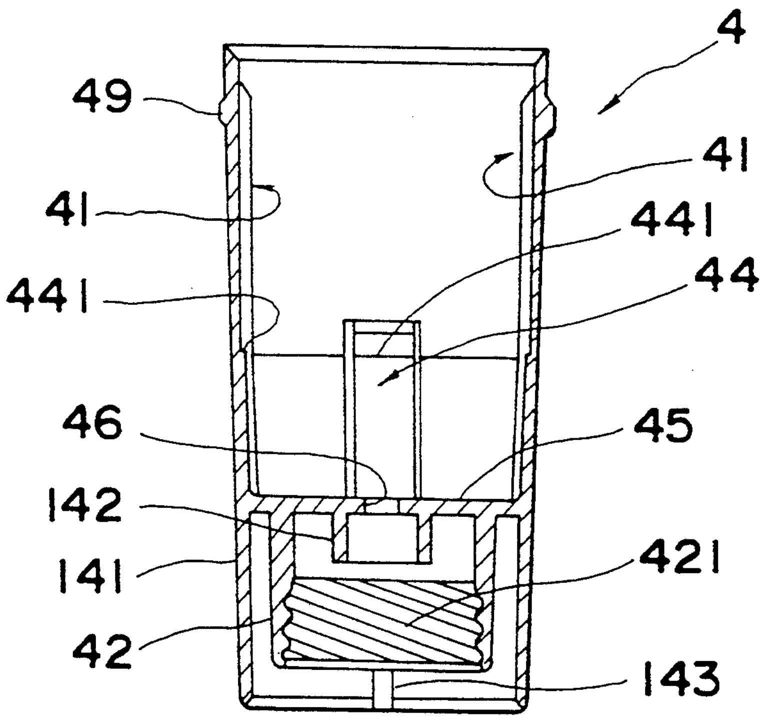
FIG. 28 is a sectional view of a guide capsule used in the fluid container of FIG. 25.
Figure 29:
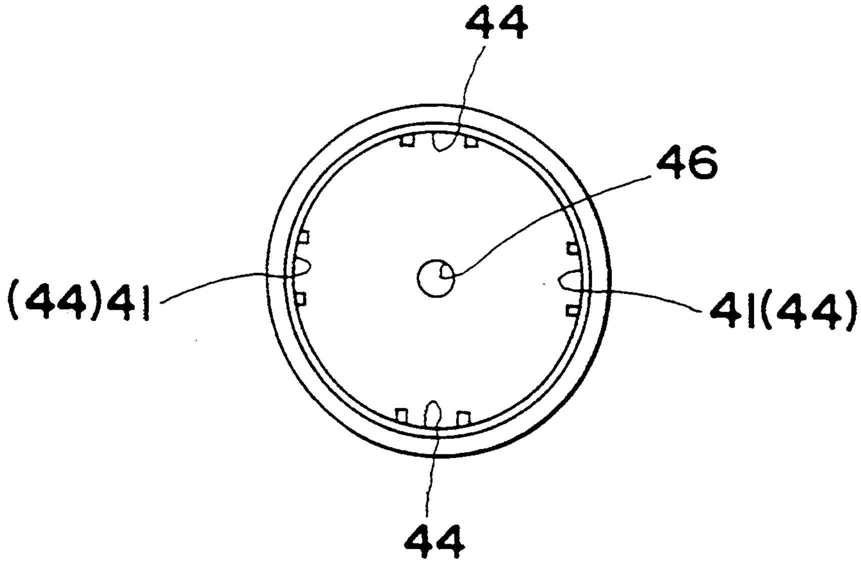
FIG. 29 is a top view of the guide capsule of FIG. 28.

As shown in FIG. 28, the guide capsule 4 is a cylindrical hollow member having a construction similar to that of the guide capsule of FIG. 1 except for that it has a skirt 141 and a cylindrical part 142 for attachment of a sealing member 144, both of which have the same axis with the connecting portion 42.

The skirt 141, surrounding the connecting portion 42, protrudes below the partition wall 45 and terminates at the shoulder 270 of the solvent container 2. The skirt 141 is fitted on the stepped portion 271 of the shoulder 270 of the solvent container 2 to strengthen the connection between the guide capsule 4 and solvent container 2. Also, the skirt 141 is provided at its lower end with projections 143 adapted to be fitted in the grooves 28 of the solvent container 2 to prevent the guide capsule 4 from disengagement from the solvent container 2. The cylindrical part 142 for attachment of the sealing member 144 protrudes below the partition wall 45 and terminates above the tapered end of the mouth 21A of the solvent container 2.

The sealing member 144 is a cap-like member, usually of an elastic material, having a hole with a diameter smaller than that of the lower piercing needle 33 of the double-pointed hollow needle 3. As shown in FIG. 25, the sealing member 144 is arranged in a space formed between the needle guide 260 of the solvent container 2, the cylindrical part 142 of the guide capsule 4 and the partition wall 45 of the guide capsule 4. This may be done by fitting the sealing member 144 on the needle guide 260 of the solvent container 2, inserting it into the cylindrical part 142 of the guide capsule 4 until it comes in contact with the partition wall 45 of the guide capsule 4.

The guide capsule 4 is provided with a female screw 421 in the inner wall of its connecting portion 42 for engagement with the male screw 211 of the solvent container 2.

Figure 30:
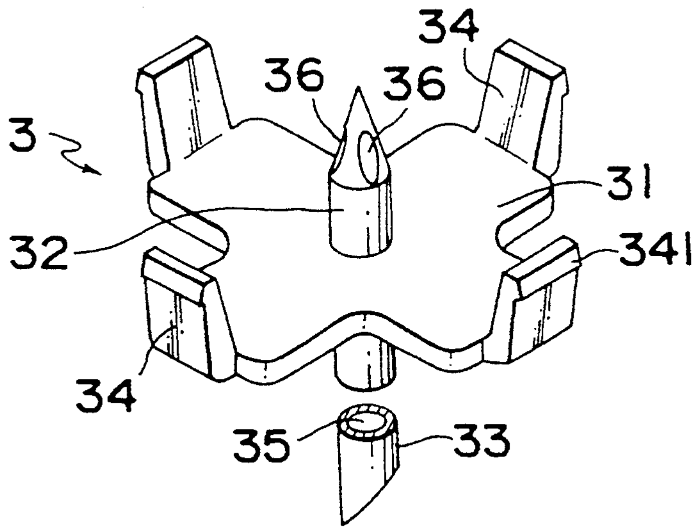
FIG. 30 is a perspective view of a double-pointed hollow needle used in the fluid container of FIG. 25.
Figure 31:
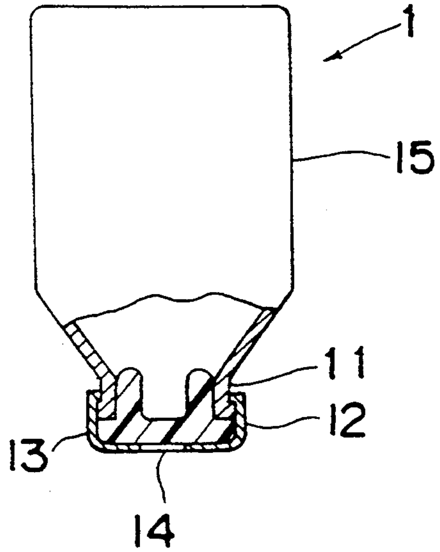
FIG. 31 is a partial cut-away side view of a drug container used in the fluid container of FIG. 25.

The double-pointed hollow needle 3 is held in the guide capsule 4 and arranged between the drug container 1 and the solvent container 2. The double-pointed hollow needle 3 is composed of a cannula 30 having a hub 31 attached to its middle part. The cannula 30 is a slender, double-pointed hollow member having a passage 35 extending from its lower bevelled edge to the upper tapered sharp end at which it is communicated with three outlet holes 36, as shown in FIG. 30. The other parts of the needle including the hub 31 are the same as those of the needle used in the embodiment of FIG. 1. Thus, there would be no need to repeat detailed explanation of the hub 31.

Figure 32:
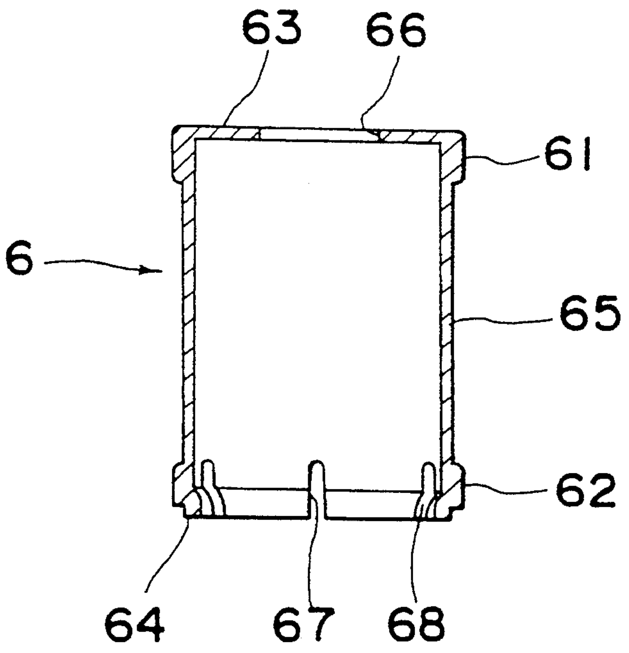
FIG. 32 is a sectional view of a vial guide used in the fluid container of FIG. 25.
Figure 33:
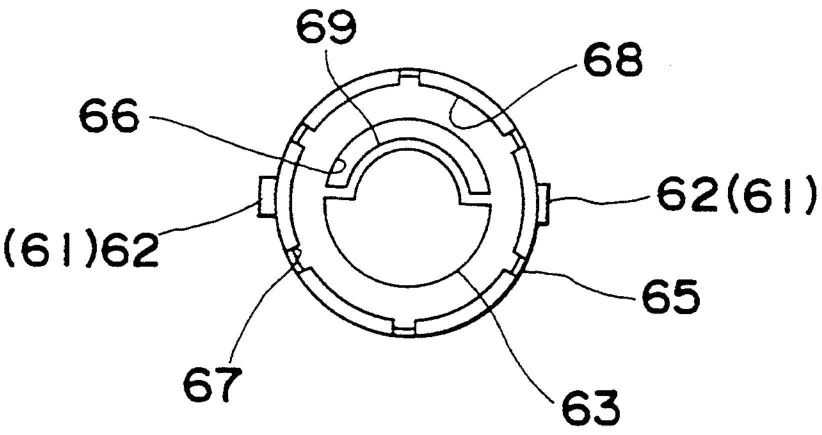
FIG. 33 is a bottom view of the vial guide of FIG. 31.
Figure 34:
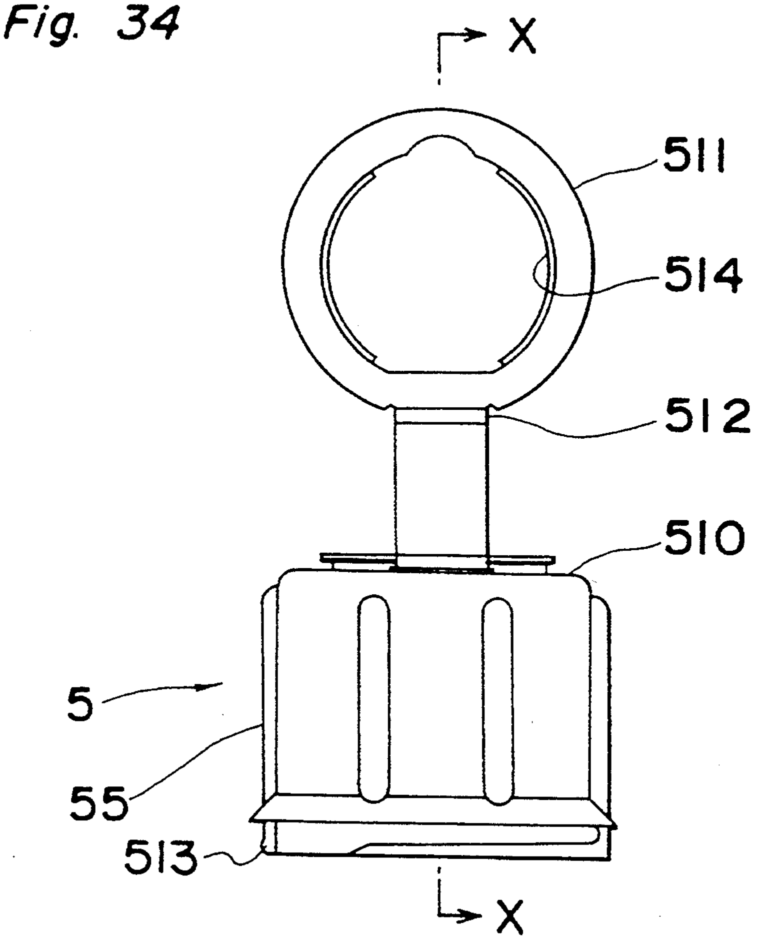
FIG. 34 is a sectional view of a cap used in the fluid container of FIG. 25.

As can be seen from FIGS. 32 to 34, the vial guide 6 is a cylindrical hollow member having the same structure as that of the vial guide of FIG. 1 except for that it has a semicircular tab 69 for removing the vial guide from the drug container 1 after use.

Figure 35:
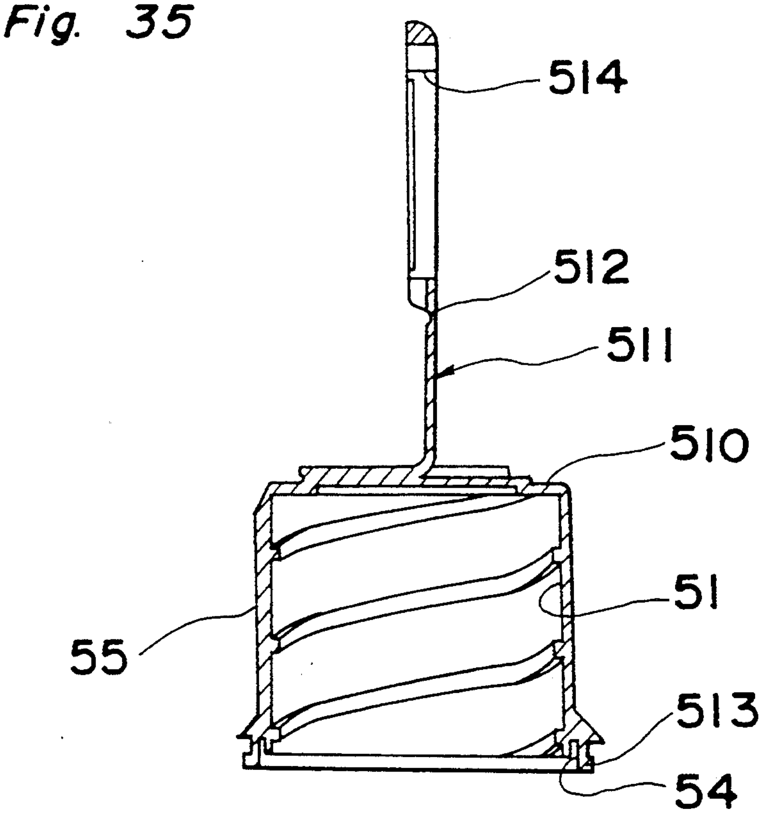
FIG. 35 is a sectional view of the cap taken along the line x—x in FIG. 34.
Figure 36:
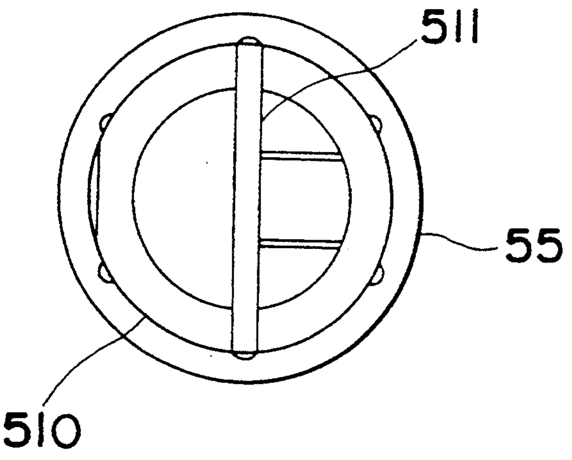
FIG. 36 is a top view of the cap of FIG. 36.

As shown in FIGS. 34 and 35, the cap 5, serving both as a hermetic sealing means for the guide capsule 4 and as a means for driving the drug container 1 downwardly in cooperation with the vial guide 6 and guide capsule 4, is a cylindrical hollow member, usually of the same material as that the guide capsule 4. The cap 5 is provided at its lower end of its skirt 55 with an annular groove 54 in which a sealing member 53 is fitted to form a hermetic seal between the cap 5 and the guide capsule 4.

In the inner wall of the skirt 55 of the cap 5 there are provided two spiral grooves 51 adapted to be engaged with the respective first projections 61 of the vial guide 6. The spiral grooves 51 run spirally along the inner wall of the cap 5 from the top end to the lower end. These spiral grooves 51 form a means for driving the drug container 1 downwardly together with the first and second projections 61 and 62 of the vial guide 6 and the vertical guide grooves 41 of the guide capsule. The spiral grooves 51 may be replaced with spiral projections formed on the inner wall of the cap 5. In this case, the first projections 61 of the vial guide 6 are so arranged that each projection 61 comes in contact with the lower side of the spiral projection.

The cap 5 is further provided at its top 510 with a hanging ring 511 to hang the fluid container on a suitable hook at its hole 514. The hanging ring 511 may be provided with a hinge joint 512 to make it foldable. If the cap 5 is used in combination with a cap-release member 8, the cap 5 may be provided at the lower end of its skirt 55 with a projection 513 adapted to be engaged with the groove of the cap-release member 80 of FIG. 25.

Figure 37:
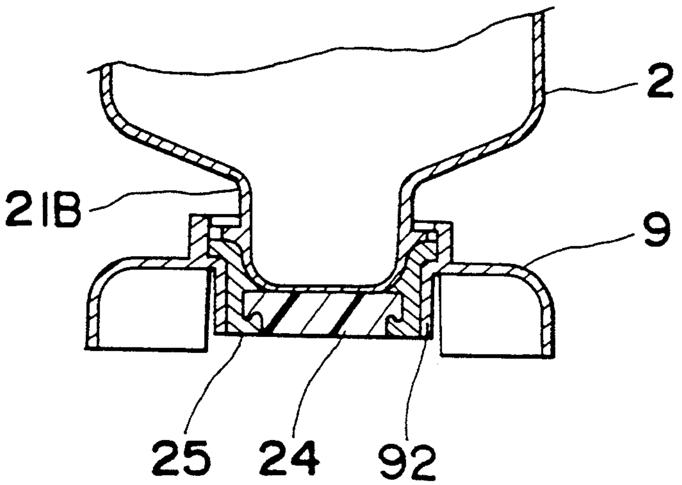
FIG. 37 is a sectional view illustrating a part of a modified form of the solvent container of FIG. 25.
Figure 38:
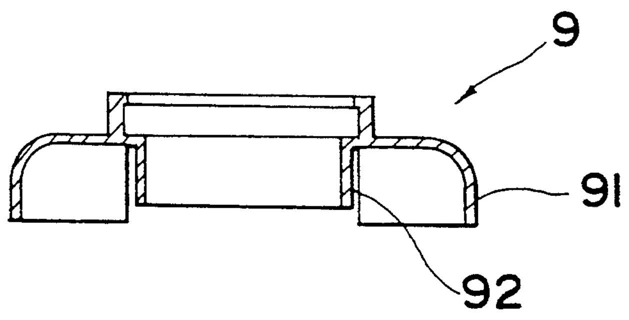
FIG. 38 is a sectional view of a stand used in the embodiment of FIG. 37.
Figure 39:
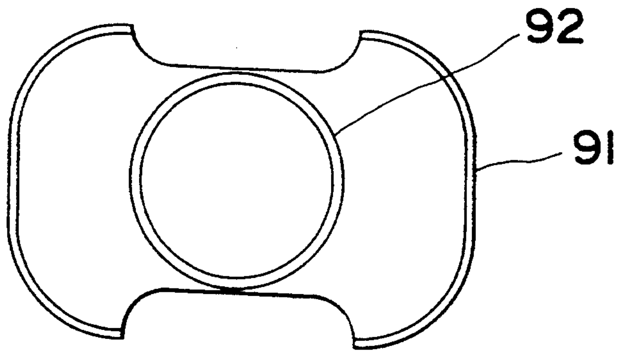
FIG. 39 is a bottom view of the stand of FIG. 37.

To set up the fluid container of the above embodiment, the solvent container 2 may have a stand 9 as shown in FIG. 37. As illustrated in FIG. 37 to 39, the stand 9 comprises a pedestal 91 and a cylindrical portion 92 for engagement with the mouth 21B of the solvent container 9. This stand 9 is usually of a metal or synthetic resin, but it may be made with any other materials into any desired structure. The attachment of the stand 9 to the solvent container is carried out by fitting the mouth 21 of the solvent container 2 in the cylindrical portion 92 of the stand 9 as shown in FIG. 37.

The above fluid container is operated in the same manner as the embodiment of FIG. 1 except for the following points.

After mixing the drug with the solvent, the fluid container is hung on a hanger at its hanging ring 511 and the resultant drug solution in the drug container 1 is returned to the solvent container 2, if necessary, by a pumping action. After this, the solvent container 2 is connected to an infusion set by piercing a needle of the infusion set into the rubber stopper 24 on the mouth 21 of the solvent container 2.

When the fluid container is to be disposed after use, the fluid container can be classified into two or more kinds of parts by material in the same manner as that of the embodiment of FIG. 1.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A fluid container comprising:

a drug container having a barrel and a narrow mouth sealed by a rubber stopper, and including first and second engaging means arranged around said barrel;

a deformable solvent container of a synthetic resin having at least one mouth sealed by a sealing means;

a cylindrical guide capsule having an open end at one end and at the other a connecting portion coupled to the mouth of said solvent container, said guide capsule being provided at an inner wall thereof with an engaging means for engagement with the second engaging means of said drug container;

a double-pointed hollow needle having a sharp piercing edge at each end and being slidably held in said guide capsule and arranged between the mouth of said drug container and that of the solvent container;

a cylindrical cap rotatably mounted on said guide capsule to seal an open end thereof as well as to hold the drug container therein, said cap being provided at an inner wall thereof with an engaging means for engagement with the first engaging means of said drug container, wherein one of said first engaging means of said drug container and the engaging means of said cap includes at least one spiral groove and projection for engaging said spiral groove, and wherein one of said second engaging means of said drug container and the engaging means of said guide capsule includes at least one vertical guide groove and projection for engaging said vertical guide groove, whereby said drug container is forced to move linearly without causing rotary motion thereof toward said solvent container when said cap is rotated, thereby allowing said double-pointed hollow needle to pierce said rubber stopper of the drug container and said sealing means of the solvent container to make a fluid communication between said drug container and solvent container through said needle.

2. The fluid container according to claim 1, wherein the first engaging means of said drug container is at least one first projection formed on an outer surface of said drug container close to the bottom thereof and engaged with a spiral groove formed in an inner wall of the cap, and wherein said second engaging means of said drug container being at least one projection formed on the outer wall of said drug container close to a shoulder portion thereof and engaged with vertical guide groove provided in an inner wall of said guide capsule.

3. The fluid container according to claim 1, wherein said guide capsule includes a means for removing said cap.

4. The fluid container according to claim 1, wherein said needle is composed of a slender pointed hollow member and a hub having arms, and wherein said guide capsule is provided with one or more needle guide grooves for slidably holding said arms of the hub.

5. The fluid container according to claim 1, wherein said solvent container has two mouths provided respectively at both ends, one of said mouths being sealed by a sealing membrane and coupled to said guide capsule, while the other mouth being sealed by a sealing means.

6. The fluid container according to claim 5, wherein said cap includes a hanging means for hanging the fluid container on a hook.

7. The fluid container according to claim 5, wherein said solvent container includes a stand fitted on the opposite mouth thereof to allow the fluid container to stand by itself.

8. The fluid container according to claim 5, wherein said guide capsule includes a means for removing said cap.

9. The fluid container according to claim 1, wherein said drug container has a cylindrical vial guide fitted thereon and having at one end an open end and at the opposite end a closed bottom, said first and second engaging means being provided on an outer wall of said vial guide.

10. The fluid container according to claim 9, wherein the first engaging means of said vial guide is at least one spiral groove formed on an outer surface thereof and engaged with a projection formed on an inner surface of said cap.

11. The fluid container according to claim 10, wherein the second engaging means of said vial guide being at least one projection formed on said outer wall close to the open end thereof and engaged with a vertical guide groove provided on said inner wall surface of said guide capsule.

12. The fluid container according to claim 9, wherein the first engaging means of said vial guide is at least one first projection formed on an outer surface of said vial guide close to the bottom thereof and engaged with a spiral groove formed in an inner wall of the cap.

13. The fluid container according to claim 12, wherein the second engaging means of said vial guide is at least one vertical guide groove formed in the outer wall of said vial guide and engaged with a projection provided on an inner wall of said guide capsule.

14. The fluid container according to claim 12, wherein the second engaging means of said vial guide is at least one second projection formed on the outer wall of said vial guide close to the open end thereof and engaged with vertical guide grooves provided in an inner wall of said guide capsule.

15. The fluid container according to claim 14, wherein said vertical guide grooves of said guide capsule are provided parallel to the center axis of the guide capsule in the inner wall of the guide capsule.

16. The fluid container according to claim 14, wherein said vertical guide grooves of said guide capsule are provided by pairs of vertical ribs formed parallel to the center axis of the guide capsule on the inner wall of the guide capsule.

17. A fluid container comprising:

a drug container having a mouth sealed by a rubber stopper;

a deformable solvent container of a synthetic resin having at least one mouth sealed by a sealing means;

a double-pointed hollow needle having a sharp piercing edge at each end;

a cylindrical guide capsule having an open end at one end and at the other end a connecting portion removably connected to said solvent container, whereby said double-pointed hollow needle being slidably held between the mouth of said drug container and that of said solvent container, said guide capsule being provided at an inner wall thereof with one or more vertical guide grooves for guiding said drug container;

a cylindrical cap having at least one spiral groove and being rotatably attached to said guide capsule to seal the open end thereof; and a vial guide having first and second projections provided on an outer surface thereof and holding said drug container therein, said vial guide being movably held in said cap in such a manner that said first and second projections of the vial guide are respectively engaged with said spiral groove of the cap and said vertical guide grooves of the guide capsule, thereby constituting a driving means for converting a rotary motion of said cap to a linear motion of said drug container without causing rotary motion of said drug container and for allowing said double-pointed hollow needle to pierce said rubber stopper of the drug container and said sealing means of the solvent container to make a fluid communication between said drub container and solvent container through said needle.

18. The fluid container according to claim 17, wherein said double-pointed hollow needle is provided with two passages.

19. The fluid container according to claim 17, wherein said double-pointed hollow needle is provided with one passage.

20. The fluid container according to claim 17, wherein said needle is composed of a slender pointed hollow member and a hub having arms, said arms being slidably arranged in needle guide grooves formed in an inner wall of the guide capsule.

21. The fluid container according to claim 20, wherein each needle guide grooves of the guide capsule is provided with a stepped portion.

22. The fluid container according to claim 21, wherein each arm of the hub is provided with a small outwardly protruding portion, said protruding portion of each arm resting on said stepped portion of said guide capsule and allowed to be disengaged from the stepped portion only when a load applied to the needle by the drug container exceeds a predetermined value.

* * * * *